(12) United States Patent
Sano et al.

(10) Patent No.: US 10,589,092 B2
(45) Date of Patent: Mar. 17, 2020

(54) METHODS FOR ENHANCING AND MODULATING REVERSIBLE AND IRREVERSIBLE ELECTROPORATION LESIONS BY MANIPULATING PULSE WAVEFORMS

(71) Applicant: The Board of Trustees of the Leland Stanford Junior University, Palo Alto, CA (US)

(72) Inventors: Michael Sano, Los Altos Hills, CA (US); Lei Xing, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 164 days.

(21) Appl. No.: 15/616,737

(22) Filed: Jun. 7, 2017

(65) Prior Publication Data
US 2017/0348525 A1 Dec. 7, 2017

Related U.S. Application Data

(60) Provisional application No. 62/346,903, filed on Jun. 7, 2016.

(51) Int. Cl.
*A61N 1/32* (2006.01)
*A61B 18/12* (2006.01)
(Continued)

(52) U.S. Cl.
CPC .......... *A61N 1/327* (2013.01); *A61B 18/1206* (2013.01); *A61B 18/14* (2013.01); *A61B 18/1402* (2013.01); *A61B 2018/0094* (2013.01); *A61B 2018/00577* (2013.01); *A61B 2018/00613* (2013.01); *A61B 2018/00732* (2013.01); *A61B 2018/00761* (2013.01); *A61B 2018/126* (2013.01)

(58) Field of Classification Search
CPC .......... A61N 1/327; A61B 2018/00613; A61B 18/1206; A61B 18/14; A61B 18/1402; A61B 2018/00577; A61B 2018/00732; A61B 2018/00761; A61B 2018/0094; A61B 2018/126
See application file for complete search history.

(56) References Cited

U.S. PATENT DOCUMENTS

| 8,814,860 B2 | 8/2014 | Davalos |
| 8,926,606 B2 | 1/2015 | Davalos |

(Continued)

*Primary Examiner* — Linda C Dvorak
*Assistant Examiner* — James A Cipriano
(74) *Attorney, Agent, or Firm* — Lumen Patent Firm

(57) ABSTRACT

A ratio of reversible electroporation and irreversible electroporation may be controlled by selecting a symmetric waveform or asymmetric waveform to either minimize or enhance irreversible effects on cells in the target tissue. Combined reversible and irreversible electroporation includes inserting one or more therapeutic electrodes into a target tissue, introducing an electroporation compound into the target tissue, selecting a pulse waveform that is either 1) asymmetric bipolar that has positive and negative pulses with different durations, or 2) symmetric bipolar that has positive and negative pulses with the same duration, and delivering to the target tissue a series of electrical pulses having the selected pulse waveform.

12 Claims, 17 Drawing Sheets

(51) Int. Cl.
 *A61B 18/14* (2006.01)
 *A61B 18/00* (2006.01)

(56) References Cited

U.S. PATENT DOCUMENTS

| | | |
|---|---|---|
| 8,992,517 B2 | 3/2015 | Davalos |
| 9,198,733 B2 | 12/2015 | Neal, II |
| 2010/0030211 A1 | 2/2010 | Davalos |
| 2012/0109122 A1* | 5/2012 | Arena ................... A61B 18/14 606/41 |
| 2013/0253415 A1 | 9/2013 | Sano |
| 2013/0345697 A1 | 12/2013 | Garcia |
| 2014/0363881 A1* | 12/2014 | Caiafa ...................... H03K 3/57 435/285.2 |
| 2015/0088120 A1 | 3/2015 | Garcia |

* cited by examiner

METHODS FOR ENHANCING AND MODULATING REVERSIBLE AND IRREVERSIBLE ELECTROPORATION LESIONS BY MANIPULATING PULSE WAVEFORMS

CROSS-REFERENCE TO RELATED APPLICATIONS

This application claims priority from U.S. Provisional Patent Application 62/346,903 filed Jun. 7, 2016, which is incorporated herein by reference.

FIELD OF THE INVENTION

The present invention relates generally to methods and devices for electroporation. More specifically, it relates to techniques for controlling the ratio of reversible vs. irreversible electroporation.

BACKGROUND OF THE INVENTION

Electroporation is a promising technique for the treatment of inoperable solid tumors either through enhancement of chemotherapy uptake using reversible electroporation, (RE) or through cell death using irreversible electroporation (IRE).

Electroporation involves application of external electric fields to tissue, increasing the voltage drop across cell membranes. This process is not instantaneous and typically takes 1-5 microseconds for the membrane potential to increase from baseline to a steady state maximum. When this potential reaches a critical potential (approximately 0.5-1 V) the molecules in the cell membrane deform in an attempt to minimize the energy in the system. This results in the formation of nanoscale defects (electro-pores) which are either transient and do not affect cell viability (reversible electroporation), or permanent and result in cell death (irreversible electroporation).

Reversible and irreversible electroporation are both useful tools in biology, cancer therapy, and other clinical applications. Conventional commercialized methods for implementing clinical reversible electroporation for electro-chemotherapy and electrogenetherapy include the Cliniporator. Conventional commercialized techniques for implementing clinical irreversible electroporation include the NanoKnife.

However, reversible and irreversible electroporation effects typically have uncontrolled overlap, resulting in undesired side-effects. A major unsolved challenge is controlling the extent/ratio to which these effects occur.

For example, reversible electroporation is useful for enhancing drug delivery and gene uptake in vivo. In this process, electrical pulses are used to create temporary defects in cell membranes which enable the uptake of macromolecules. Under certain circumstances, these electrical pulses result in irreversible (IRE) damage to the cells resulting in a focal ablation zone within the tissue. In electro-chemotherapy and electro-gene therapy, significant volumes of tissue may be irreversibly damaged when the clinical intent is to maximize molecular uptake and minimize cell death.

In contrast, when irreversible tissue ablation is desired, the clinical effect is typically limited to an internal volume of complete cell killing surrounded by a region of reversibly electroporated tissue. Irreversible electroporation uses high intensity electrical pulses to focally ablate solid tumors. Clinically, two or more needle electrodes are advanced around a target tumor. A series of approximately 100 electrical positive polarity pulses 1000 to 3000 V in amplitude and 50 to 100 µs in duration are then delivered to disrupt the membranes of cells within a well-defined volume. FIG. 1A shows a pulse waveform for IRE treatments, using a series of long duration positive polarity pulses. These electrical pulses increase cell transmembrane potentials (TMP) above a critical threshold and create permanent nanoscale defects which result in rapid cell death. IRE ablations exhibit a characteristic sub-millimeter translation from complete cell killing to unaffected tissue due to the exponential decrease in electric field intensity in tissue far from the electrodes.

Though IRE is a promising emerging procedure, there are some clinical challenges which may slow widespread adoption of the therapy. The long duration electrical pulses create local and systemic muscle contractions and may inadvertently interact with cardiac rhythms. To alleviate this, patients must receive significant doses of chemical paralysis and pulse delivery is synchronized with the heart beat to ensure pulses are delivered during the absolute refractory period. Additionally, the ablation zone produced by IRE is dependent on local dynamic electrical properties of the tissue and heterogeneities can potentially distort the electric field and produce irregular shaped ablations.

High frequency irreversible electroporation (H-FIRE) is a new protocol which replaces the long duration monopolar IRE pulses with a burst of alternating polarity pulses between 250 ns and 5 µs to alleviate muscle contractions caused by longer duration pulses and produce more predictable ablations. FIG. 1B show a pulse waveform for H-FIRE treatments, using multiple bursts containing 0.25 to 5 µs alternating polarity pulses.

However, previous reports indicate that H-FIRE produces smaller ablations than IRE; reversible electroporation using HF waveforms has yet to be reported clinically.

BRIEF SUMMARY OF THE INVENTION

The present invention provides a method for electrical pulse delivery in which the ratio of RE to IRE is controlled by selection of the positive and negative pulse widths to either enhance or minimize irreversible effects. For example, new asymmetric waveforms suited for specific treatment protocols and clinical applications are described. These waveforms enable the practitioner to tune the extent of reversible and irreversible electroporation. This method can be used to produce volumes which are free from irreversible damage. Alternatively, this method can be used to produce volumes which are completely ablated as well as combinations of these two extremes. This method can be used to produce irreversible electroporation ablations which are equivalent to those produced by existing clinical IRE systems with the added benefits of eliminating muscle contractions and producing more uniform ablations in heterogeneous tissue.

The use of asymmetric waveforms can be used to create significantly larger H-FIRE ablations. The lethal thresholds for primary and metastasized brain cancer cells were 42% lower for asymmetric waveforms compared to equivalent energy symmetric waveforms.

The reversible electroporation threshold was 54% lower than the lethal threshold for symmetric waveforms and 33% lower for asymmetric waveforms, indicating that waveform symmetry can be used to tune the relative sizes of reversible and irreversible ablation zones.

The techniques of the present invention overcome challenges with electroporation including the elimination of muscle contractions and production of more predictable ablation volumes in vivo. They can be used to improve in vivo gene therapy, delivery of chemotherapeutics, delivery of large molecules across the blood brain barrier, and the ablation of solid tumors.

The technique has applications to electro-chemotherapy, electro-genetherapy, irreversible electroporation (bulk tumor ablation), blood brain barrier disruption, and synthetic biology (gene transfection).

The techniques of the present invention provide the ability to produce equivalent ablation sizes as commercial irreversible electroporation techniques while eliminating muscle contractions seen in vivo and producing ablations which more closely match analytical predictions. It also provides the ability to tune reversible ablation zones to enhance drug or gene delivery to large volumes while minimizing or eliminating lethal effects. It has the ability to enhance drug delivery across the blood brain barrier while having a minimal effect on healthy brain tissue. It also has the ability to improve gene transfection efficiency and minimize cell killing.

In one aspect, the invention provides a method for combined reversible and irreversible electroporation, the method comprising: inserting one or more therapeutic electrodes into a target tissue; introducing an electroporation compound into the target tissue; selecting a pulse waveform that is either 1) asymmetric bipolar that has positive and negative pulses with different durations, or 2) symmetric bipolar that has positive and negative pulses with the same duration; and delivering to the target tissue a series of electrical pulses having the selected pulse waveform; whereby a ratio of reversible electroporation and irreversible electroporation may be controlled by selecting a symmetric waveform or asymmetric waveform, respectively, to either minimize or enhance irreversible effects on cells in the target tissue.

The selection of the pulse waveform may include selecting an energy delivered in each burst, a number of bursts delivered, and selecting the asymmetric bipolar waveform or symmetric bipolar waveform.

The delivering to the target tissue a series of electrical pulses may include delivering a burst energized for 100-1000 microsecond 1 to 100 times with a 0.1 to 100 Hz repetition rate between bursts, whereby mostly necrotic cell death surrounded by reversibly electroporated cells is produced.

The delivering to the target tissue a series of electrical pulses may include delivering a burst energized for 0.2-100 microseconds delivered 100 to 10,000 times with a 0.1 to 1000 Hz repetition rate between bursts, whereby mostly apoptotic cell death surrounded by reversibly electroporated cells is produced.

A selected symmetric waveform may have positive and negative pulses of the same voltage magnitudes. The positive and negative pulses may have the same duration of 0.1 to 10 microseconds, or may have different durations, each with a duration of 0.1 to 10 microseconds. In some implementations, a total on-time duration of positive pulses is the same as a total on-time duration of negative pulses.

A selected asymmetric waveform may have positive and negative pulses of different voltage magnitudes. The positive and negative pulses may have the same duration of 0.1 to 10 microseconds, or may have different durations, each with a duration of 0.1 to 10 microseconds. In some implementations, a total on-time duration of positive pulses is different than a total on-time duration of negative pulses.

A selected asymmetric waveform may have a delay between positive pulses between 0.01 and 1000 microseconds.

The delivering to the target tissue the series of electrical pulses may include delivering pulses for 0.2 to 2000 microseconds by sequentially repeating the series of alternating positive and negative pulses. The delivering to the target tissue the series of electrical pulses may include delivering pulses at a voltage between 1 and 10,000 V. The delivering to the target tissue the series of electrical pulses may include delivering pulses at a frequency of 0.01 to 1,000,000 Hz (preferably between 0.1 and 1000 Hz). The delivering to the target tissue the series of electrical pulses may include delivering pulses sequentially 2 to 10,000 times, preferably 2-1000 times.

The electrodes may have various configurations. Two independent electrodes (source and sink) may be inserted into the target tissue. Three or more independent electrodes may be inserted into the target tissue and combinations of one or more electrodes act as an electrical source and a combination of one or more electrodes act as electrical sinks. One electrode may act as the electrical source and is inserted into the target tissue and a grounding pad placed on the skin acts as the electrical sink. Two or more electrodes may be inserted into the target tissue and energized simultaneously (all electrical sources) and a grounding pad on the skin acts as the electrical sink. Two or more electrodes may be inserted into the target tissue and energized independently and a grounding pad on the skin acts as the electrical sink. One electrode may be an array of smaller conductors acting as an electrical source and a grounding pad on the skin acts as the electrical sink. One electrode may be an array of smaller conductors acting as an electrical source and a separate electrode on the same probe acts as an electrical sink. Two or more electrode arrays of smaller conductors may act as electrical sources and sinks.

The electrodes may be used to deliver the compound directly to the target site. The compound may be delivered systemically, or the compound may exist naturally in the target tissue or media. The compound may be a fluid cooled at or below body temperature, or may be warmed at or above body temperature. The compound may be a highly conductive fluid (0.3 to 2.0 S/m) such as phosphate buffered saline, normal saline, Lactated Ringers solution, Viaspan (UW solution), or another conductive isotonic solution. The compound may have a low conductivity (0.001 to 0.3 S/m) such as deionized water or deionized water with dissolved solids, proteins, or ions required to make it isotonic. The compound may contain DNA, RNA, RNAi, SiRNA, genes, endonucleases, amino acids, polypeptides, proteins, or other biological compounds which change the behavior or genetic code of cells. Example proteins include Cas3, Cas8a, Cas5, Cas8b, Cas8c, Cas10d, Cse1, Cse2, Csy1, Csy2, Csy3 GSU0054, Cas10, Csm2, Cmr5, Cas10, Csx11, Csx10, Csfl, Cas9, Csn2, Cas4 Cpfl, C2c1, C2c3, C2c2. CRISPR-Cas9, CRISPR-DR2, CRISPR-DRS, CRISPR-DR6, CRISPR-DR8, CRISPR-DR9, CRISPR-DR19, CRISPR-DR41, CRISPR-DR52, CRISPR-DR57, CRISPR-DR65, DRACO (Double-stranded RNA Activated Caspase Oligomerizer), zinc-finger nucleases, transcription activator-like nucleases. The compound may contain a chemotherapy intended to induce necrosis, apoptosis, or DNA damage. Example compounds include Anthracyclines, doxorubicin (Adriamycin) epirubicin (Ellence), Taxanes, paclitaxel (Taxol), docetaxel (Taxotere), 5-fluorouracil, Cyclophosphamide, Carboplatin, Docetaxel, Paclitaxel Platinum agents (cisplatin, carboplatin), Vinorelbine (Navelbine), Capecitabine (Xeloda), Liposomal doxorubicin (Doxil), Gemcitabine (Gemzar), Mitoxantrone (Novantrone), Ixabepilone (Ixempra), Albumin-bound paclitaxel (nab-paclitaxel or Abraxane), Eribulin (Halaven). The compound may contain molecules intended to give the target tissue a new biological function or induce the production of specific molecules. The compound may contain a drug intended to treat a specific disease or stimulate the production of a compound. Examples include up-regulation of the production of insulin by pancreatic cells in diabetic patients.

The target tissues of the methods of the invention may be mammalian cells, eggs, zygotes, embryos, Prokaryotes (bacteria or archaea), Eukaryotes (protozoa, algae, fungi), or yeast grown in in vitro culture or suspension. The target tissues may be cells in blood, serum, plasma, urine, bile, lymph, semen, or other biological fluids. The target tissues may be cancers growing in healthy organs. Example cancers include prostate cancer, breast cancer, liver cancer, kidney cancer, bladder cancer, bone cancer, brain cancer, skin cancer, and other cancers of the bone, blood, lymphatic system, or soft tissues. The target tissue may be diseased tissue or healthy tissue.

In another aspect, the invention provides an apparatus for combined reversible and irreversible electroporation, the apparatus including: therapeutic electrodes for insertion into a target tissue a computer controller for generating a pulse waveform that is, selectively, either 1) asymmetric bipolar that has positive and negative pulses with different durations, or 2) symmetric bipolar that has positive and negative pulses with the same duration; a hardware controller for generating high voltage electrical pulses to the therapeutic electrodes in accordance with the generated pulse waveform; such that a ratio of reversible electroporation and irreversible electroporation can be controlled by selecting a symmetric waveform or asymmetric waveform, respectively.

The apparatus may also include a high voltage capacitor bank comprising four switches to create an H-Bridge configuration for delivering positive and negative polarity pulses from a single high voltage power supply. It may include two switches in a totem pole configuration for delivering positive and negative polarity pulses from a positive and negative power supply. The apparatus may include a transformer in conjunction with an H-Bridge or totem pole configuration to step up a lower voltage to a higher voltage.

The switches may comprise MOSFET, SiC MOSFET, IGBT, or relay switches. Each switch may include two or MOSFETs, SiC MOSFETs, IGBTs, or relays in series to increase the voltage that each switch can withstand. Each switch may include two or more MOSFETs, SiC MOSFETs, IGBTs, or relays in parallel to increase the current that each switch can deliver. Each switch may be made up of two or more components in parallel and two or more components in series to increase the voltage and current that each switch can deliver.

The apparatus may include a high voltage source connected to a capacitor bank of one or more capacitors in a series-parallel arrangement. The apparatus may include a high voltage source connected to a single high voltage capacitor.

DETAILED DESCRIPTION OF THE INVENTION

Figure 1A:
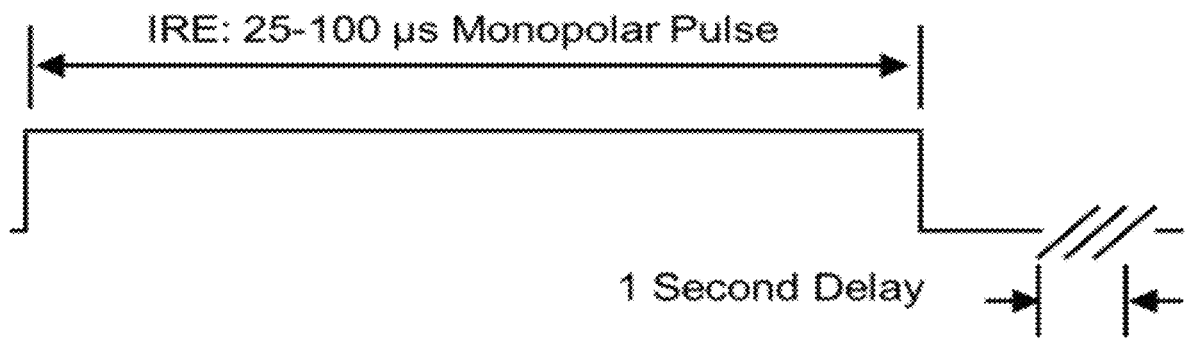
FIGS. 1A-B are voltage vs. time graphs showing conventional pulse waveforms for IRE and H-FIRE protocols.
Figure 1B:
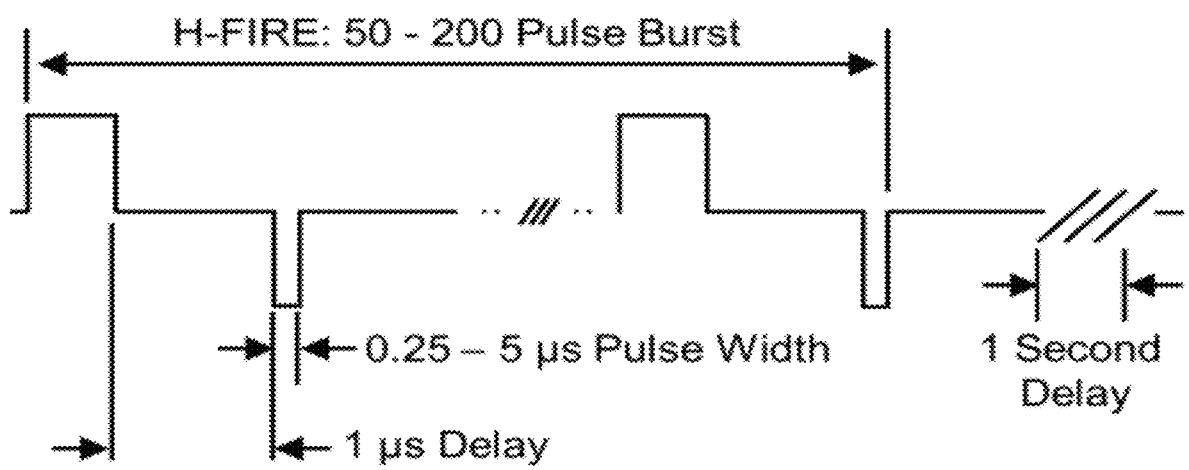

Embodiments of the present invention provide an electroporation method for tuning the reversible and lethal effects to maximize one while minimizing the other. This is accomplished by selecting the pulse waveform in such a way that one phenomena dominates over the other.

Preferred embodiments and further teachings related to the present invention are described below in reference to the drawing figures.

Figure 2A:
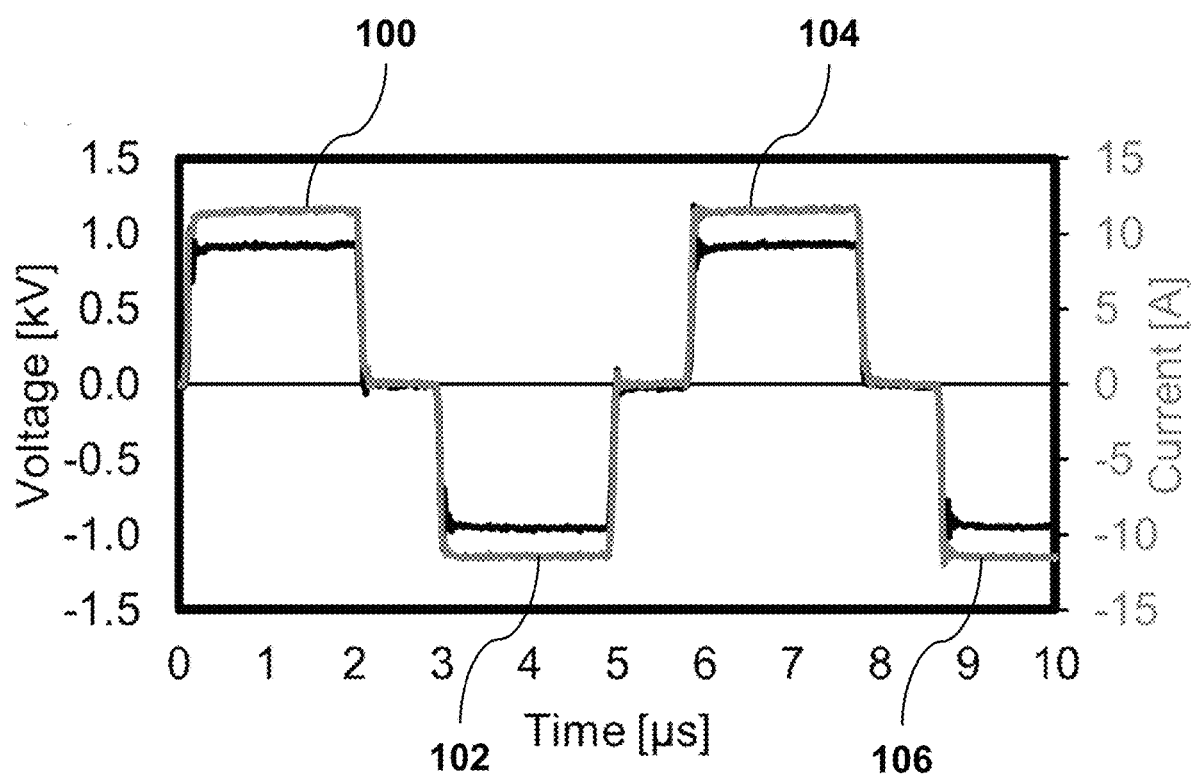
FIG. 2A is a graph of voltage and current vs. time, illustrating symmetric pulses, according to an embodiment of the invention

In one embodiment, a method of electroporation may be used as part of a clinical workflow for gene transfection, electrochemotherapy, and/or CRISPR. An appropriate anesthetic plane is established to allow the physician to insert one or more therapeutic electrodes into the target tissue. This tissue could be a tumor for oncology, healthy or poorly functioning pancreatic tissue for diabetes treatment, brain tissue for the treatment of Parkinson's or other neurological disorders, bone or bone marrow for immunotherapy, skin for the treatment of dermatitis, skin diseases, and infection or fertilized egg/zygote/embryo for genetic engineering purposes. The desired compound, e.g., gene sequence, silencing RNA, or chemotherapy, is then injected into the patient either systemically through the vasculature or directly into the treatment zone. If injected directly into the treatment site, the therapeutic electrodes can be used as the delivery tool. The clinician then inserts electrodes into or around the target volume and delivers a series of symmetric electrical pulses. FIG. 2A is a graph of voltage and current vs. time, illustrating symmetric pulses 100, 102, 104, 106 that minimize cell death while improving uptake of large molecules into the cell.

The pulse bursts include between 2 and 1000 electrical pulses which alternate in polarity between positive and negative voltage and current, i.e., pulse 100 is positive, 102 is negative, 104 is positive, 106 is negative. Each pulse 100, 102, 104, 106 is of equal duration and can be between 10 ns and 1 ms (preferably between 100 ns and 10 µs). Each treatment includes the delivery of 1-1000 bursts (preferably 1-100) delivered at a repetition rate between 0.001 Hz and 1000 Hz (preferably 0.1-10 Hz).

The treatment electrodes can either be a pair (source and sink) of electrodes inserted directly into the treatment site, multiple pairs (sources and sinks), a single electrode and distant grounding pad, tweezers placed around the target tissue, or electrodes inserted into the vasculature designed to treat an entire organ or specific volume of tissue.

Figure 2B:
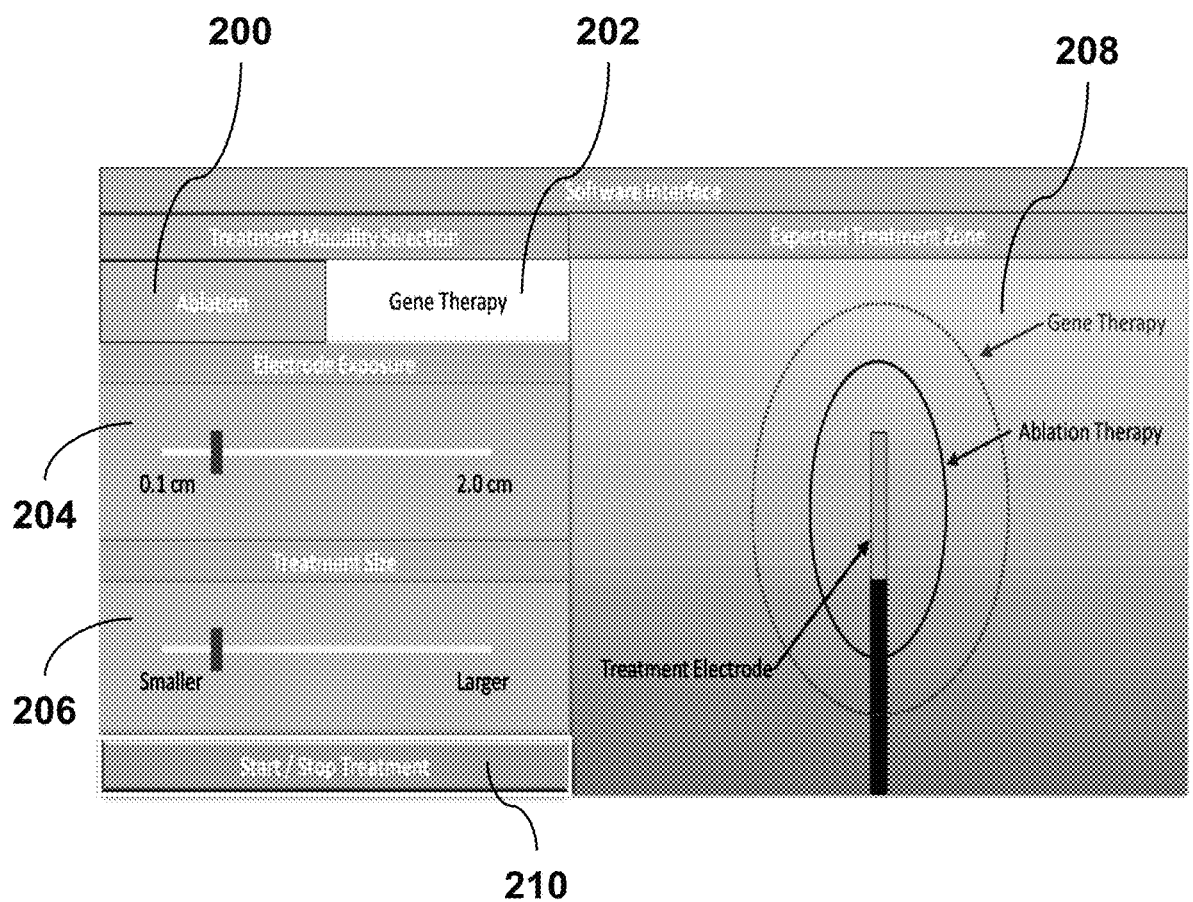
FIG. 2B is an image of a graphical user interface of a clinical system for electroporation, according to an embodiment of the invention.

The clinician may use a software interface on the device to program the volume of tissue treated. An example software interface is shown in FIG. 2B. The physician selects the type of treatment desired (e.g., ablation 200, gene therapy 202) and the computer will automatically select the appropriate waveform to deliver. The physician selects which electrode configuration being used (electrode exposure 204 and treatment size 206) and a graphical panel 208 displays the anticipated treatment volume. Conversely, the physician may increase or decrease the target volume and the computer will determine which voltages and pulse parameters should be used. The physician will then press a 'start button 210 or foot pedal to initiate treatment using pulse waveforms according to the principles of the present invention, as will be described in more detail below. The system will then automatically deliver the appropriate treatment and monitor the electrical properties (impedance, resistance, conductivity) of tissue. This information can be used to determine appropriate treatment endpoints as well as monitor for arcing, heating, or other deleterious effects. After the electrical bursts are delivered, the treatment is finished and the physician removes the electrodes and closes and incisions made.

In another embodiment, a method of electroporation may be used as part of a workflow for laboratory or in vitro gene transfection, electrochemotherapy, and/or CRISPR. Target cells can be treated in suspension, while they are adhered to the surface of a well plate, while they are in a 3D engineered tissue matrix (matrigel, collagen, agarose, etc.), or in situ in an ex-vivo organ.

Adherent cells are released from the culture plate via trypsonization, centrifuged, washed, and suspended in a transfection buffer containing the desired gene sequences or RNA. The buffer/cell suspension is injected into an electroporation cuvette containing source and sink electrodes on opposing sides of the cuvette. Electrodes can be separated by 0.1-10 cm (preferably 0.1-1 cm). A series of symmetric pulse bursts are then delivered across the cuvette using pulse waveforms according to the principles of the present invention, as will be described in more detail below. The cells are then removed from the cuvette and returned to normal culture conditions.

The culture media above adherent cells is removed and replaced with a transfection buffer containing the desired gene sequences or RNA. Electrodes are then inserted into the culture well into contact with the bottom of the well plate. A series of electrical bursts are then delivered through the electrodes. The transfection buffer is then removed and normal culture media is added to the cells. Alternatively, cells can be cultured in well plates which are engineered to have embedded electrodes along the sides/bottom of the well plate. This process is identical for cells grown in a 3D tissue model.

Figure 3A:
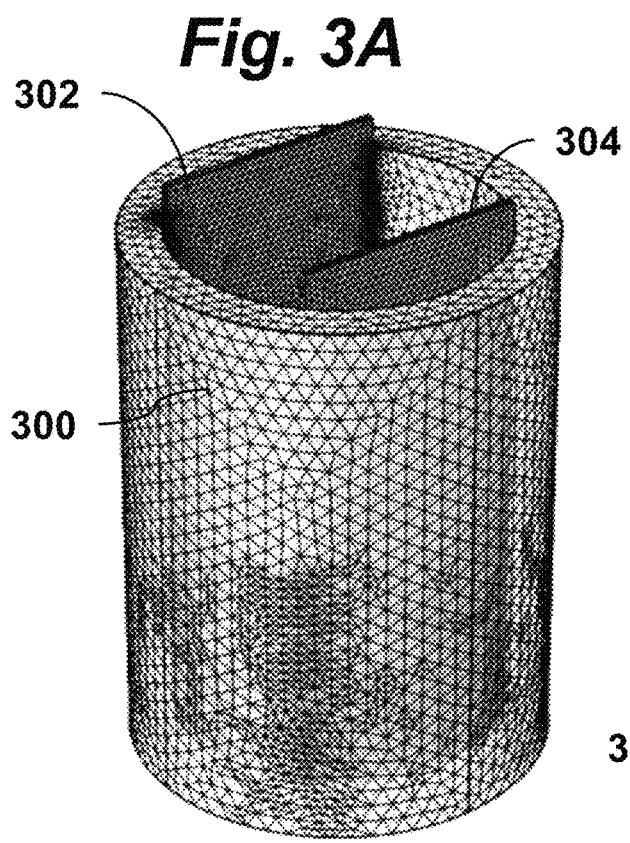
FIGS. 3A-B are isometric and top-down views of a cell culture well with two electrodes inserted, according to an embodiment of the invention.
Figure 3B:
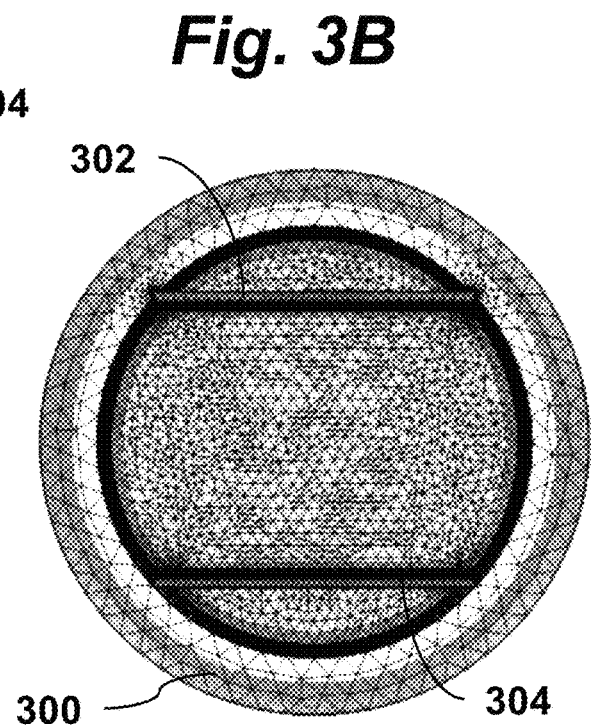
Figure 3C:
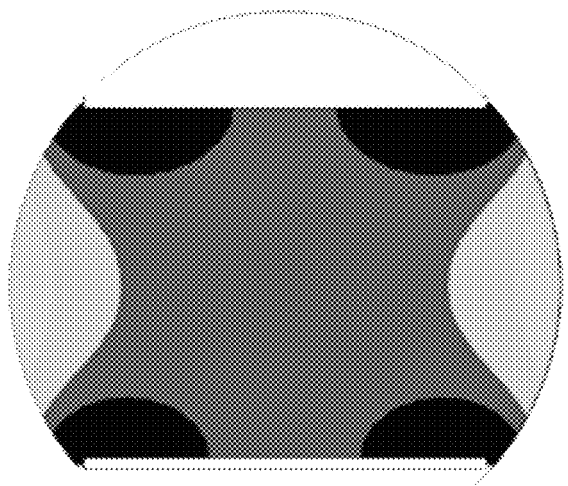
FIG. 3C illustrates a finite element simulation showing the electric field distribution, according to an embodiment of the invention.
Figure 3D:
FIG. 3D is an image showing adherent cells which were exposed to an electric field, according to an embodiment of the invention.

FIGS. 3A-D illustrate stages of an in vitro technique for treating adherent cells according to an embodiment of the present invention. FIG. 3A is an isometric view of a cell culture well 300 with two electrodes 302, 304 inserted. FIG. 3B is a top-down view of a cell culture well with two electrodes inserted. The electrodes extend from outside of the well to the bottom well surface and enable the delivery of electrical energy to the cells attached to the well's bottom surface. FIG. 3C illustrates a finite element simulation showing the electric field distribution within the well when 1180V is applied between the plates. Isocontour boundaries between shaded regions depict electric field strengths of 2000V/cm, 1750 V/cm, 1500 V/cm, and 1250 V/cm. FIG. 3D is an image showing adherent cells which were exposed to a sufficient electric field to become electroporated adjacent to unaffected cells. The cells in FIG. 3D were exposed to 1180V pulses indicating that electroporation occurred between 1500 and 1750 V/cm.

Figure 4:
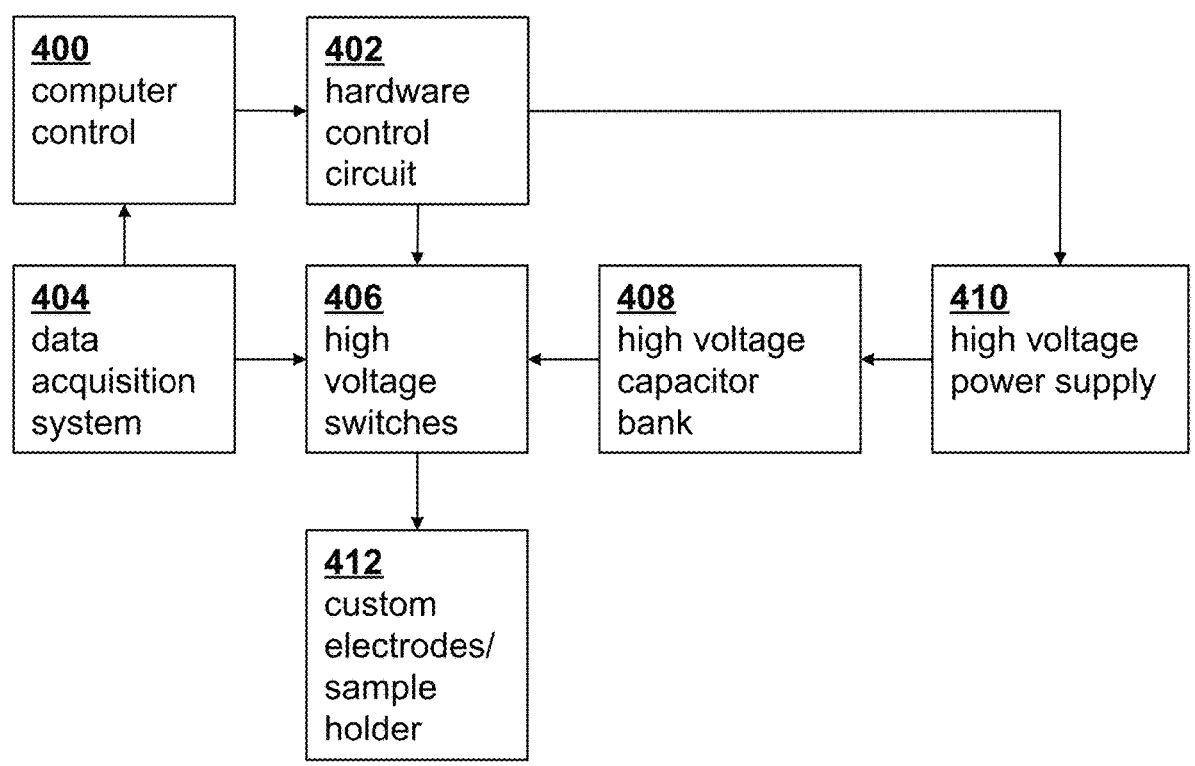
FIG. 4 is a schematic block diagram of a system for delivering electroporation treatment using pulse waveforms according to the principles of the present invention.

FIG. 4 is a schematic block diagram of a system for delivering electroporation treatment using pulse waveforms according to the principles of the present invention. The pulse delivery system includes a computer controller 400 connected to hardware control circuit 402 and a data acquisition system 404. The computer 400 has a graphical user interface (FIG. 2B). The hardware control circuit 402 has a microcontroller or field programmable gate array (FPGA) which is connected to the pulse delivery hardware (high voltage switches) 406 and high voltage power supply 410. In some implementations, hardware control circuit 402 may also be connected to additional circuitry such as heart beat synchronization, arc detection, over current detection, safety interconnects, logical controls, and an emergency on/off switch.

After parameters are selected using the graphical user interface, computer control 400 communicates the appropriate pulse waveform parameters (voltage, pulse lengths, number of pulses, number of bursts, repetition rate, etc.) to the hardware control circuit 402 (microcontroller/FPGA). The hardware control circuit 402 waits for an appropriate command (foot petal or button press) to start the selected treatment.

Once treatment is initiated, the hardware control circuit 402 turns on the high voltage power supply 410 which charges the high voltage capacitor bank 408 to an appropriate level. High voltage switches 406 then deliver pulse waveforms to custom electrodes 412 in contact with tissue. The system delivers the treatment and monitors for emergency stop conditions (e.g., arc, over current, button press). It may also monitor the treatment for voltage and current and adjust the high voltage supply to adequately maintain the appropriate conditions.

Figure 5:
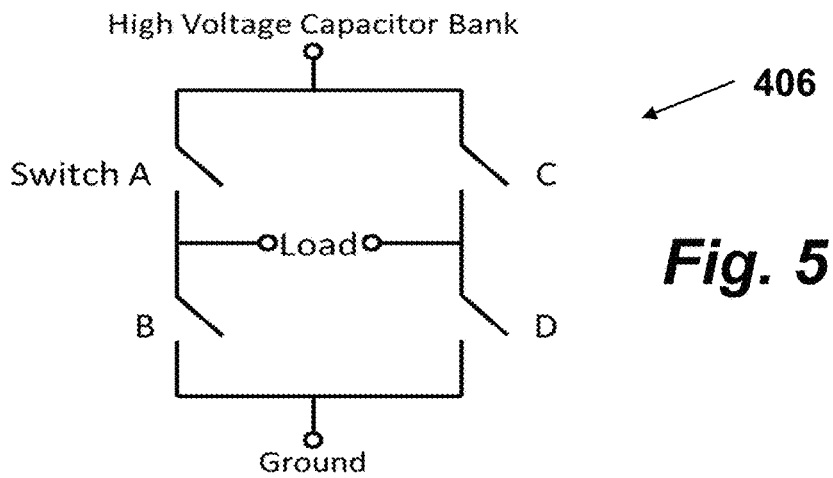
FIG. 5 is a schematic diagram of a circuit for generating high voltage symmetric and asymmetric pulse waveforms, according to an embodiment of the invention.

As detailed in FIG. 5, high voltage switches 406 have an H-Bridge configuration which contains a minimum of 4 MOSFET or IGBT switching stages (Switches A, B, C, D). Each switching stage may in turn be a series stack of 1-100 lower voltage MOSFETs or IGBTs designed to open and close at the exact same time. The four switching stages are configured in a bridged configuration such that Switch A and Switch D close simultaneously to generate a positive polarity pulse and Switch C and Switch B close simultaneously to generate a negative polarity pulse.

Figure 6:
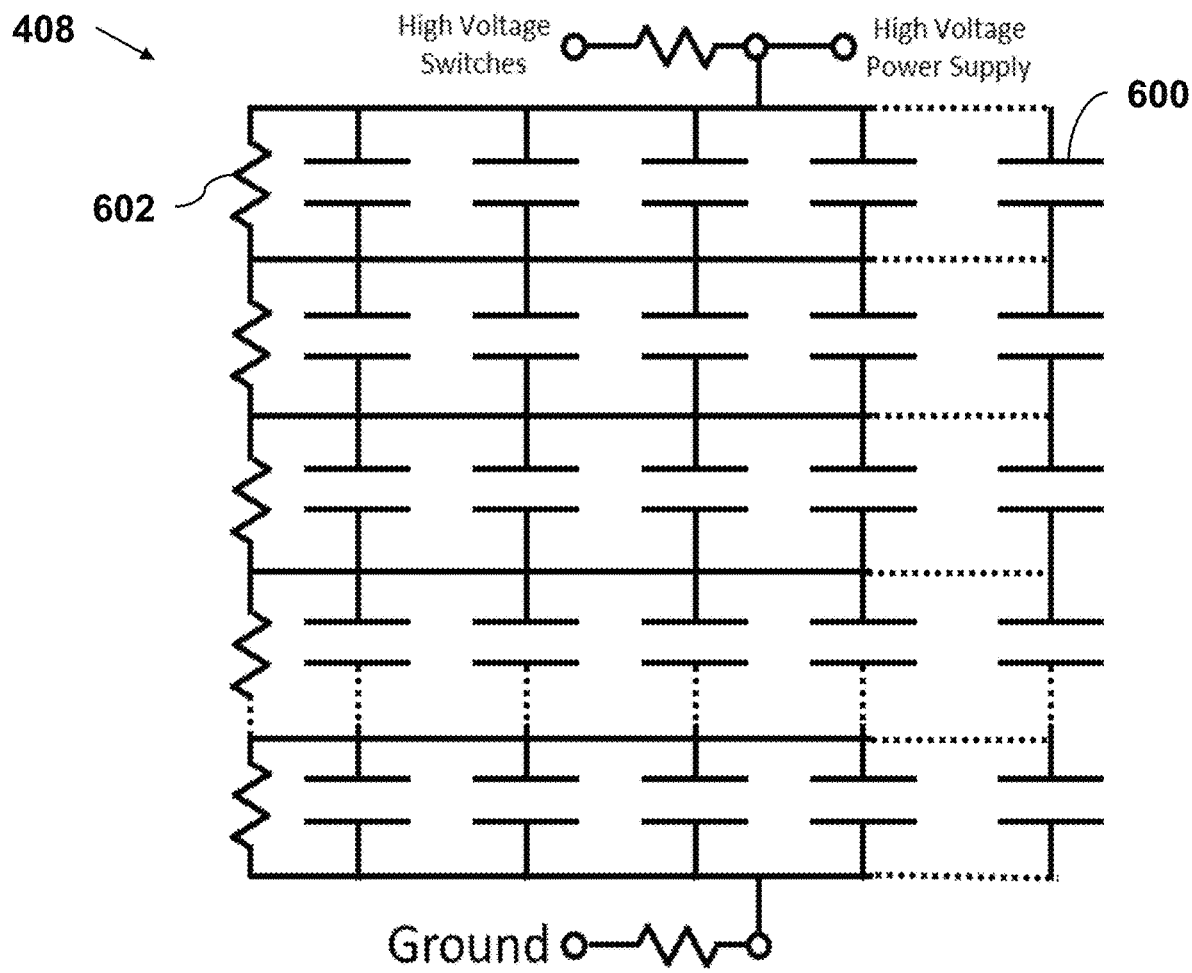
FIG. 6 is a schematic diagram of a capacitor bank architecture, according to an embodiment of the present invention.

These electroporation methods of the present invention deliver high voltages and high currents. Instantaneous power can be in excess of 0.4 megawatts. A typical power supply cannot deliver both high voltage and high current. To accomplish this, we use a low-current, high voltage power supply 410 to charge a capacitor bank 408, as described above in relation to FIG. 4. Capacitors which can withstand 2-10 kV and store large quantities of charge are expensive, and sometimes not available in the capacitance values required (15-200 microFarads). To achieve the desired output, we use a capacitor bank 408 which consists of a stack of series connected capacitors which are rated for 1000-1500 V each, as detailed in FIG. 6. By connecting them in series strings, we increase the voltage which the capacitor bank can withstand. To increase the capacitance value of the bank, we connect multiple series strings in parallel. To protect any individual capacitor 600 from experiencing a voltage above its rated voltage, we connect a high value resistor 602 (0.5-100 megaOhms) in parallel with each capacitor. These resistors also help discharge the capacitor bank to safe levels once the power has been turned off.

Figure 7A:
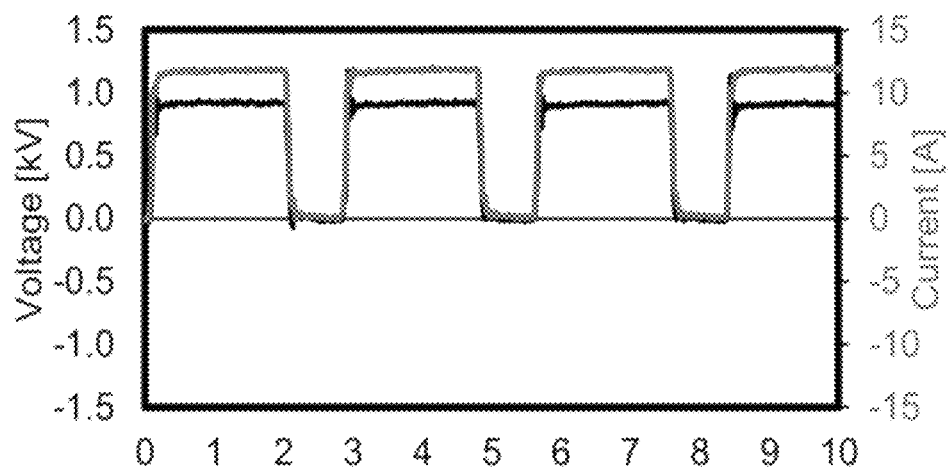
FIGS. 7A-C are graphs of voltage and current vs. time for example waveforms, showing the first 10 μs of the waveforms, illustrating the principles of the present invention.
Figure 7B:
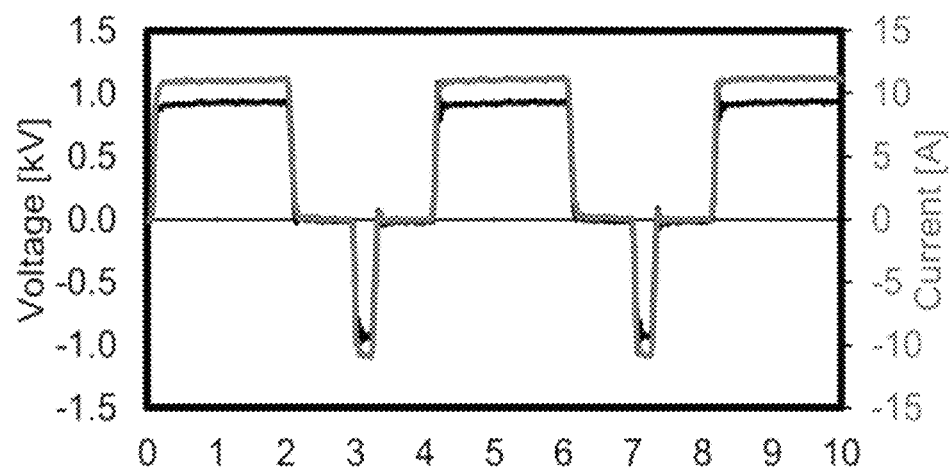
Figure 7C:
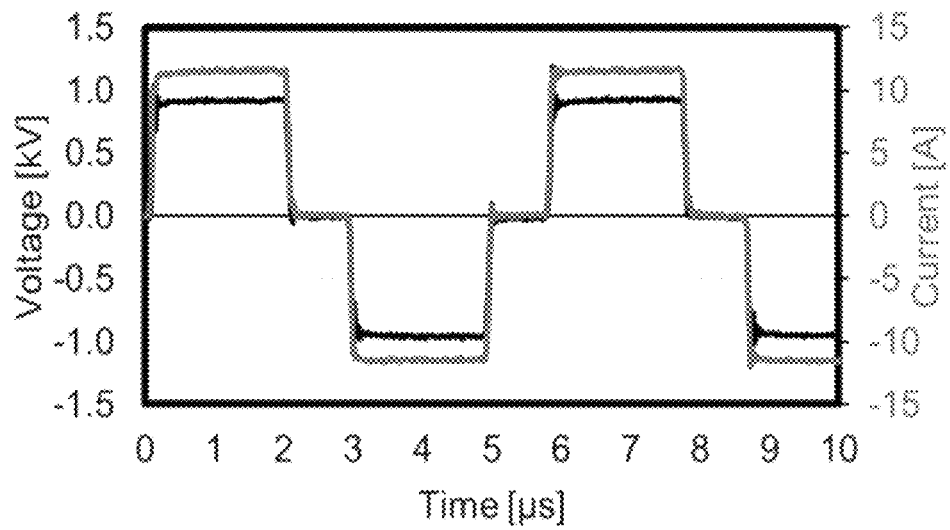

To demonstrate and illustrate the principles of the present invention, the inventors used 2D and 3D cell culture models to show that an increase in lethal threshold for H-FIRE treatments is directly tied to the symmetry of the waveform. It was discovered that the lethal threshold of H-FIRE protocols can be modulated by altering the positive and negative pulse widths. Such waveforms are illustrated in FIGS. 7A-C. Waveforms which have a higher degree of asymmetry, including positive only polarity waveforms, have lower lethal thresholds and result in larger ablation zones. The inventors also discovered that the threshold for inducing reversible electroporation is affected by waveform asymmetry and protocols can be optimized to enhance reversible electroporation while minimizing irreversible effects.

The waveforms in FIGS. 7A-C shown voltage and current vs. time for the first 10 μs of the waveforms. FIG. 7A is a waveform having 2 μs positive polarity only. FIG. 7B is an asymmetric waveform having 2 μs positive, 1 μs delay, 0.25 μs negative pulse structure. FIG. 7C is a symmetric waveform having 2 μs positive, 1 μs delay, 2 μs negative pulse structure.

In experiments, U87 primary human glioblastoma cells and MDA-MB-231 BR3 breast cancer cells isolated from murine brain metastasis were cultured to 80% confluency in standard DMEM culture media supplemented with 10% FBS and Penicillin-Streptomycin. Cells were harvested via trypsinization and seeded either directly onto the bottom of 12 well plates or in a 50% gelatinous protein mixture and culture media at a density of 100 k cells/mL. These cells were then allowed to reach confluent cultures over 4-7 days, over which time cell culture media was replaced as necessary. Prior to treatment media was removed and replaced with 2 mL of fresh culture media.

The electroporation treatments in the experiment were delivered through two blunt 16 AWG needles with a 3 mm edge-to-edge separation. A custom pulse generator was used to deliver IRE and H-FIRE protocols. Treatment protocols were either monopolar (all pulses were positive polarity, as shown in FIG. 7A), asymmetric bipolar (positive and negative pulses had different durations, as shown in FIG. 7B), or symmetric bipolar (positive and negative pulses were the same duration, as shown in FIG. 7C).

To simplify discussion of these protocols we denote pulse structures by the compact notation (P, D, N) where P indicates the positive pulse length in microseconds, N indicates the negative pulse length in microseconds, and D indicates the delay in microseconds between successive pulses. In the present context, differences of 10% or more between P and N constitute an asymmetric waveform, while differences less than 10% constitute a symmetric waveform. For example, (2, 1, 0.25) represents an asymmetric pulse waveform with a 2 μs positive pulse, followed by a 1 μs delay, then a 0.25 μs negative pulse, as shown in FIG. 7B. The notation (2, 1, 2) represents a symmetric waveform with alternating polarity 2 μs pulses separated by a 1 μs delay, as shown in FIG. 7C. All protocols in this experiment used a 1 μs delay between changes in pulse polarity.

To compare equivalent energy IRE and H-FIRE treatments, the H-FIRE waveforms were repeated in a burst such that the total energized time of each burst was equivalent to 50 or 100 μs. For example, a (1, 1, 1) waveform was repeated 25 times to produce a 50 μs burst or repeated 50 times to produce a 100 μs burst.

In cases where waveforms could not produce energized times of exactly 50 or 100 μs, the closest energized time without exceeding the target time was used. For example, the (1, 1, 0.5) waveform was energized for 49.5 μs or 99 μs by repeating the waveform 33 or 66 times, respectively, in each burst. In all treatment groups the output of the generator was set to deliver pulses which were 900 V in amplitude.

Numerical Analysis

Figure 8A:
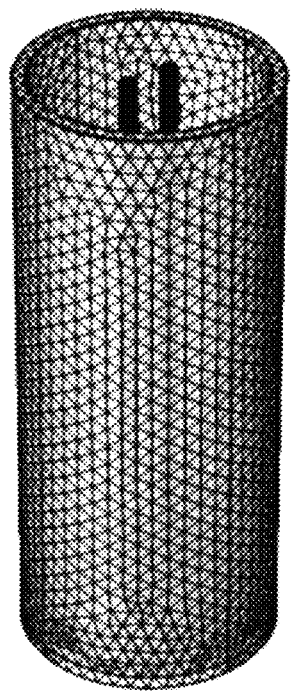
FIGS. 8A-B are perspective and top views of a mesh used to simulate an electric field distribution, according to principles of the present invention.
Figure 8B:
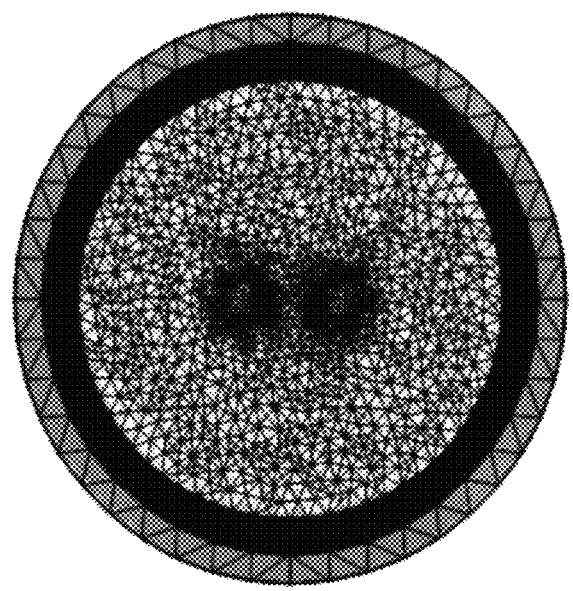

The electric field distribution within a standard 12 well chamber was modeled numerically using COMSOL Multiphysics (V5.0, COMSOL Inc., Palo Alto, Calif.) via the 3D Electric Currents module. This module solves the equations $$\nabla \cdot J = Qj, J = \sigma E + Je,$$

and $$E = -\nabla V,$$

where J is the local current density, Q is the electric charge, E is the electric field, Je is the external current density, and V is the local voltage. As shown in FIGS. 8A-B, a free tetrahedral mesh was generated in the media domain using the Extremely Fine preset while all other domains were meshed using the Normal preset values. The media domain was then refined twice using a refinement method which splits each tetrahedron along the longest edge.

Experimental voltages were applied to the top most surface of one electrode. The top surface of the adjacent electrode was set to ground (0 V). All other external boundaries were set as insulators (n·J=0). The electrical conductivity (a) was set to 1.2 S/m for the media, $2.22 \times 10^6$ S/m for the electrodes, and $1 \times 10^{-16}$ S/m for the plastic well plate components. These simulations took approximately 29 minutes to solve on an Intel i7 processor with 32 GB RAM.

Figure 8C:
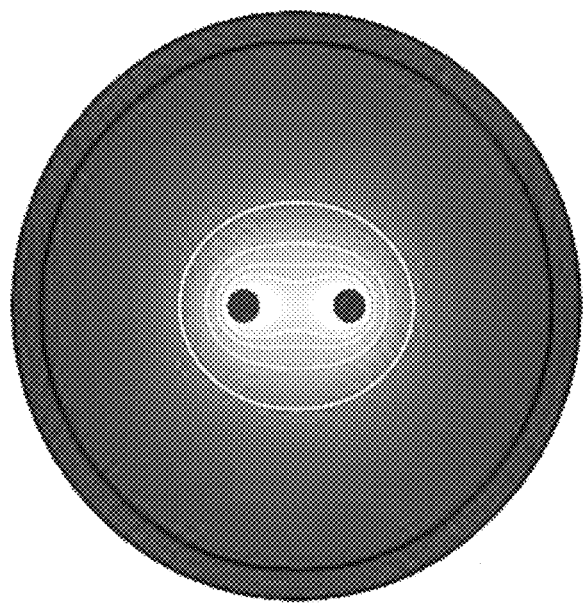
FIG. 8C is a top cross-sectional view of the electric field distribution within a well containing the mesh shown in FIGS. 8A-B.

FIGS. 8A-B are perspective and top views of a mesh used to simulate the electric field distribution within a 12-well when parallel 1 mm electrodes spaced 3 mm edge-to-edge are used to deliver 900 V. FIG. 8C is a top cross-sectional view of the electric field distribution within the well, showing electric field distributions along the x- and y-axis, where isocontour lines represent electric fields of 500, 1000, 1500, and 2000 V/cm, from outside to inside. These distributions were exported into a spreadsheet where they were used to correlate treatment geometries with electric field values.

Each treatment zone was measured and an electric field value correlating the height and width were determined. Each experimental parameter was repeated a minimum of three times (N=3) yielding at least six electric field values which were averaged and reported as mean±standard deviation. Statistical significance between groups was determined using a two sided Student's T-test with unequal variances. An alpha value of 0.01 ($\alpha$=0.01), 99% confidence interval, was used to determine if thresholds between treatment groups were statistically significantly different.

Figure 8D:
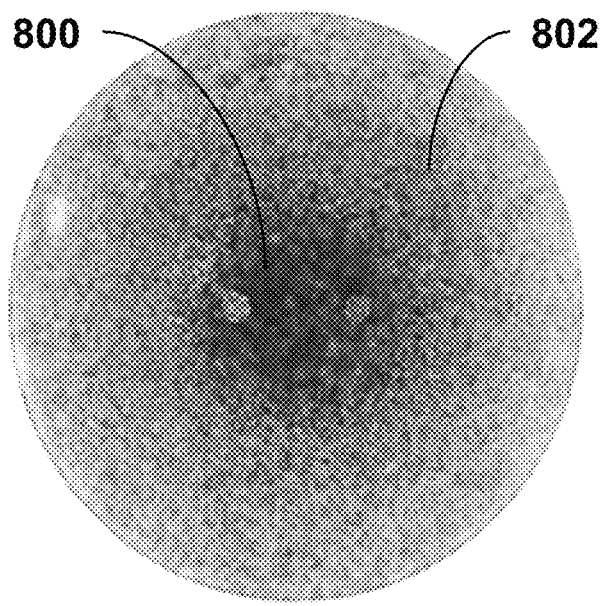
FIG. 8D is a top cross-sectional view of electroporated and unaffected cells immediately post-treatment after exposure to H-FIRE bursts, illustrating principles of the present invention.

Visual Assessment of Reversible Electroporation and Lethal Treatment Zones Stock solutions of 4 µM Calcein AM (Life Technologies, Carlsbad, Calif.) were prepared by adding 125 µL of sterile DMSO to 50 µg of powdered dye and stored at −20° C. until use. Stock solutions of propidium iodide (PI) (MP Biomedicals Inc., Burlingame, Calif.) were prepared using a concentration of 1 mg per mL sterile PBS and stored at 4° C. until use. Reversible electroporation thresholds were assessed by adding 2 µL/mL Calcien AM and 100 µL/mL of PI stock solutions to each well 5 minutes prior to treatment. The samples were imaged immediately after treatment using a fluorescence microscope with an automated stage (Leica DMI600 B, Buffalo Grove, Ill.) using Green Fluorescent Protein and Texas Red filter cubes to visualize live and dead cell populations, respectively. The height (y-axis) and width (x-axis) of each treatment zone was measured using the microscope software's built in measurement tool. FIG. 8D shows electroporated (inner region 800) and unaffected (outer region 802) MDA-MB-231 BR3 cells immediately post-treatment after exposure to 100× H-FIRE Bursts. Each burst used an asymmetric (2, 1, 0.5) waveform which was energized for 50 µs.

To assess lethal thresholds, cells were treated with IRE or H-FIRE protocols and incubated at 37° C. in 5% $CO_2$ for 24 hours. Equivalent concentrations of Calcien AM and PI stock solutions were then added to the cells and the ablation zone was imaged and measured.

Figure 9A:
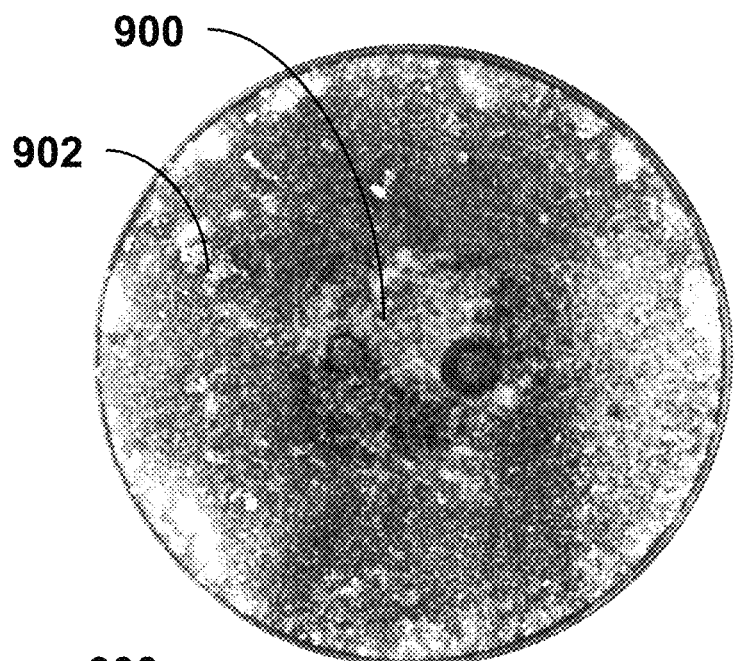
FIGS. 9A-B are images showing a comparison of ablations in 3D and 2D culture conditions, illustrating principles of the present invention.
Figure 9B:
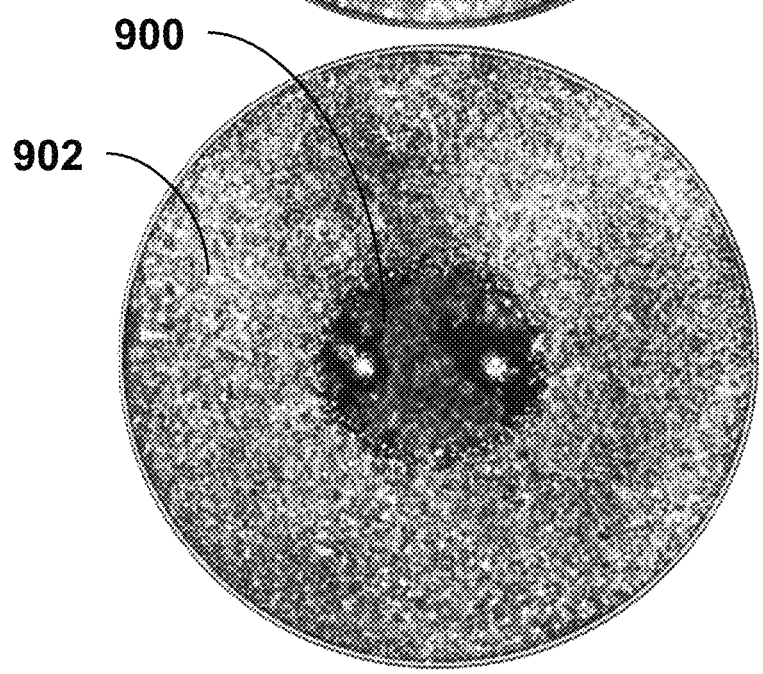

FIGS. 9A-B are images showing a comparison of ablations in 3D and 2D culture conditions. FIG. 9A is an image of U87 cells grown in 3D Matrigel. FIG. 9B is an image of U87 cells grown in 2D media-only culture conditions.

After reaching confluency, cells were exposed to H-FIRE protocols. Live (outer regions 902) and dead (inner regions 900) images were obtained 24 hours post treatment to determine the ablation geometry. For most treatment groups, there was no statistical difference in the ablation size or lethal threshold between 2D and 3D culture. However, some protocols including the (2, 1, 0.25) pulse group shown here were statistically significantly different. Both groups were exposed to 100× bursts each energized for 100 µs.

Effect of Waveform Asymmetry

Figure 10A:
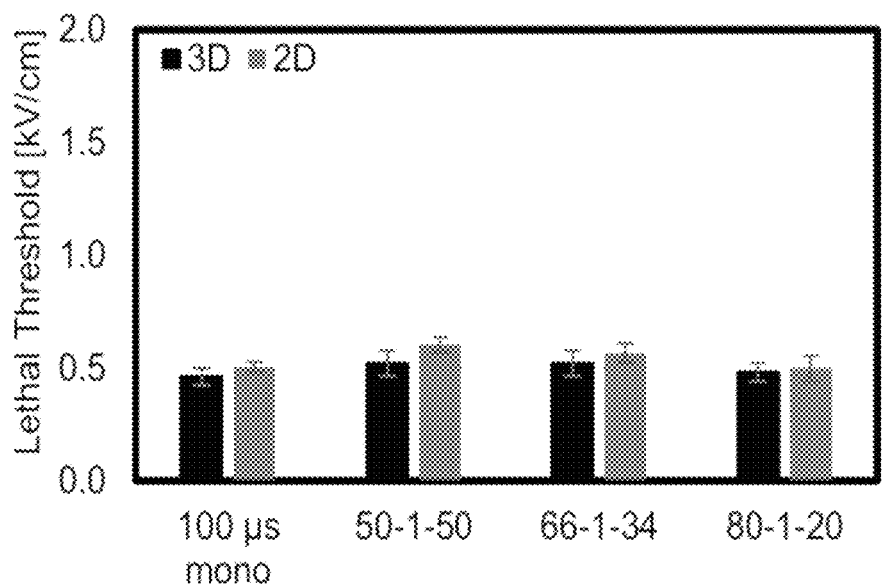
FIGS. 10A-D are plots showing that 2D vs. 3D culture conditions have minimal impact on lethal threshold, according to principles of the present invention.

Symmetric waveforms required higher electric fields to induce cell death. This effect was observed in U87 2D and 3D culture conditions, as shown in the graphs of FIGS. 10A-D. Using an asymmetric waveform had a larger impact for shorter duration (≤5 µs) pulses than for longer IRE type (≥20 µs) pulses. Monopolar 100 µs IRE treatment groups had an average lethal threshold of 484±37 V/cm. FIG. 10A is a bar graph comparing 2D and 3D lethal thresholds for long duration (>20 µs) IRE pulses which were either monopolar (100 µs) or alternated with a 1 µs delay between polarity change. When a symmetric alternating waveform (50-1-50) was delivered, the lethal threshold increased to 570±49 V/cm. Introducing asymmetry into the waveform (20, 1, 80) lowered the lethal threshold to 490±48 V/cm.

For H-FIRE treatments, symmetric waveforms had significantly higher lethal threshold than the asymmetric and monopolar waveforms. This trend existed for both 2D and 3D cultures.

Figure 10B:
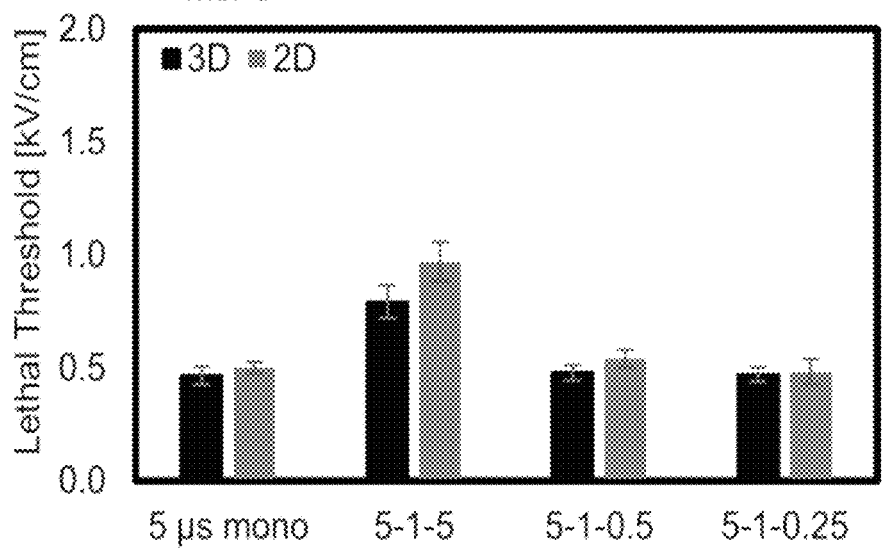

Monopolar 5 µs protocols had an average lethal threshold of 482±37 V/cm. FIG. 10B is a bar graph comparing 2D and 3D lethal thresholds for monopolar, symmetric, and asymmetric H-FIRE pulses where the longest pulse is 5 µs. This increased to 881±120 V/cm for symmetric (5, 1, 5) waveforms and decreased to 510±47 and 478±45 V/cm for the (5, 1, 0.5) and (5, 1, 0.25) asymmetric waveforms, respectively.

Figure 10C:
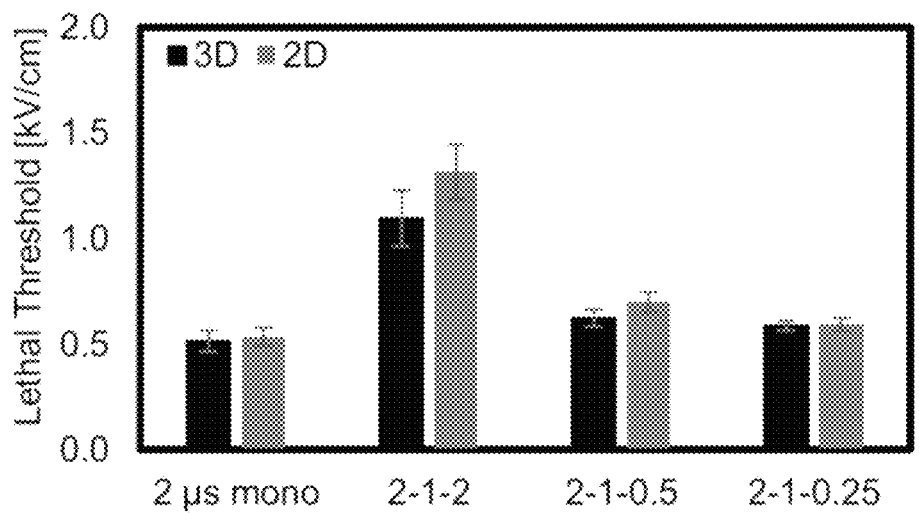

Monopolar 2 µs protocols had an average lethal threshold of 527±45 V/cm. FIG. 10C is a bar graph comparing 2D and 3D lethal thresholds for monopolar, symmetric, and asymmetric H-FIRE pulses where the longest pulse is 2 µs. This increased to 1206±170 V/cm for the symmetric (2, 1, 2) waveform and decreased to 663±57 and 592±26 V/cm for the (2, 1, 0.5) and (2, 1, 0.25) asymmetric waveforms, respectively.

Figure 10D:
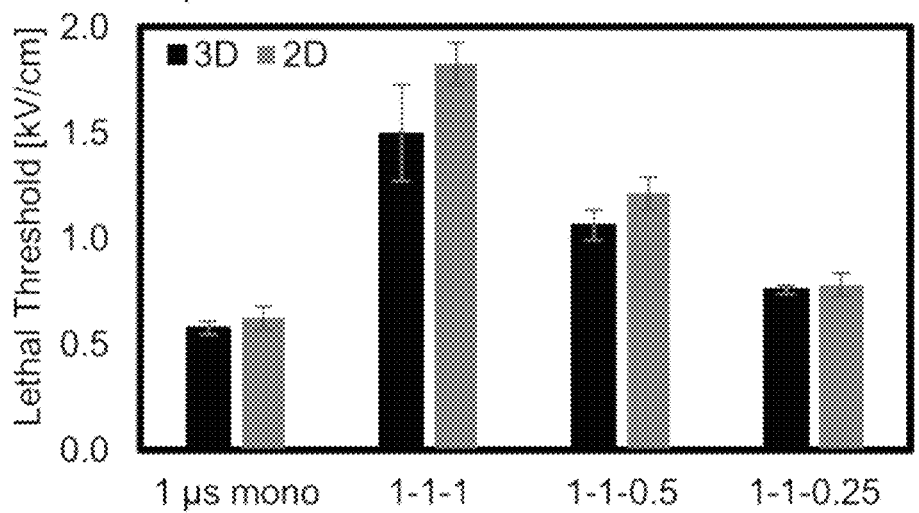

Monopolar 1 µs protocols had an average lethal threshold of 600±49 V/cm. FIG. 10D is a bar graph comparing 2D and 3D lethal thresholds for monopolar, symmetric, and asymmetric H-FIRE pulses where the longest pulse is 1 µs. This increased to 1609±260 V/cm for the symmetric (1, 1, 1) waveform and decreased to 1138±106 and 769±41 V/cm for the (1, 1, 0.5) and (1, 1, 0.25) asymmetric waveforms, respectively.

It is interesting to note that the 5 µs and 2 µs positive polarity waveforms had lethal thresholds which were close to the 100 µs monopolar waveform while the symmetric waveforms had significantly higher lethal thresholds. The lethal thresholds for the positive polarity waveforms were 484±40, 482±37, 527±45, and 600±49 V/cm for 100, 5, 2, and 1 µs monopolar waveform groups.

A total of 16 protocols were examined in both 2D monolayer cultures and 3D Matrigel cultures. All treatments delivered 100× bursts each energized for 100 µs. In 11 of 16 groups there was no statistically significant difference ($\alpha$=0.01) between the lethal thresholds found in 2D and 3D culture platforms. In the treatments which were statistically different, the mean lethal thresholds differed by an average of 16% (12-22%). In groups which were not statistically different, the mean lethal thresholds differed by an average of 8% (1-26%). Based on the similarity between these two culture platforms for U87 cells, all additional experiments were conducted only in 2D culture.

50 µs Vs. 100 µs Energized Times

Figure 11A:
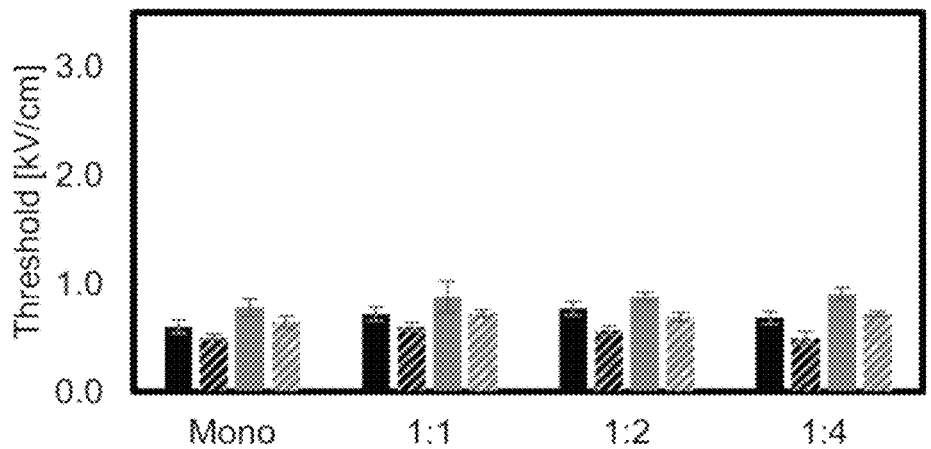
FIGS. 11A-C are bar graphs showing the impact of burst duration on lethal thresholds for different cell lines, according to principles of the present invention.
Figure 11B:
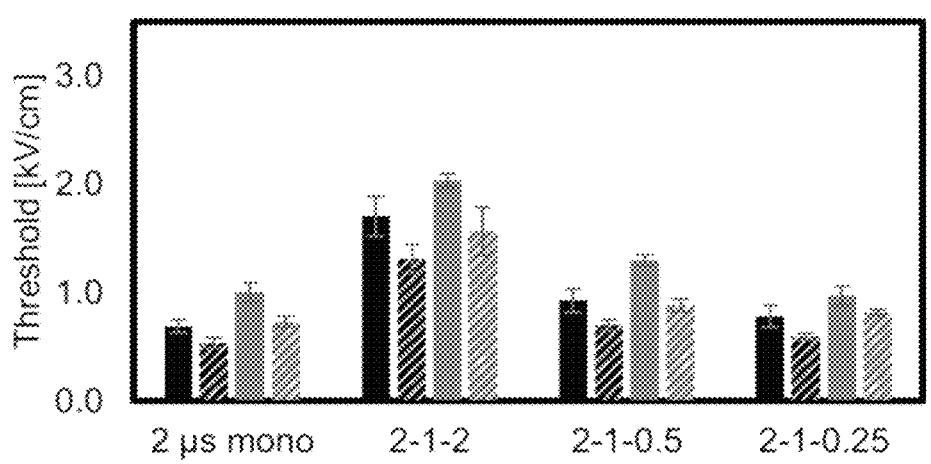
Figure 11C:
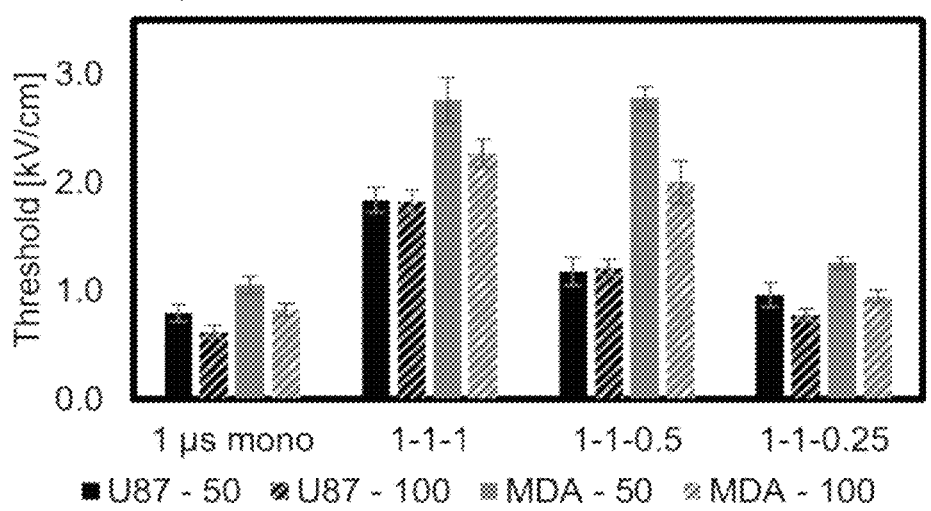

IRE is often employed clinically when tumors are in close proximity to critical nerves or blood vessels where tissue heating can result in deleterious outcomes. A simple way to minimize heating is to reduce the pulse-length (IRE) or energized time per burst (H-FIRE). FIGS. 11A-C show the impact that reducing the burst duration (and thus energy delivered) from 100 µs to 50 µs has on lethal thresholds for the MDA and U87 cell lines. All treatment groups received 100× bursts where each burst was energized for 50 µs (solid) or 100 µs (hashed). In general treatment groups the waveform with the highest degree of asymmetry had the lowest lethal threshold.

For long duration IRE pulses, monopolar pulses resulted in the lowest lethal thresholds. FIG. 11A is a bar graph showing lethal threshold for long duration (>20 µs) IRE pulses which were either monopolar (50 µs and 100 µs) or alternated with a 1 µs delay between polarity change. The ratios 1:1, 1:2, and 1:4 indicate the ratio of the positive polarity pulse to the negative polarity pulse duration. Lethal thresholds of 505±23 and 644±55 V/cm were found for U87 and MDA cells, respectively, when 100 µs monopolar pulses were used. When the pulse width was decreased to 50 µs, this lethal threshold increased to 603±63 and 779±79 V/cm for U87 and MDA cells, respectively. For these long duration pulses, symmetric and asymmetric bipolar waveforms had lethal threshold which were 14% higher than the monopolar only waveforms. Waveforms energized for 50 µs had lethal thresholds which were 20% higher on average than those energized for 100 µs.

For H-FIRE treatments, symmetric bi-polar waveforms had higher lethal thresholds than monopolar and asymmetric bi-polar waveforms for both cell types. FIG. 11B is a bar graph showing lethal thresholds for monopolar, symmetric, and asymmetric H-FIRE pulses where the longest pulse was 2 µs. FIG. 11C is a bar graph showing lethal thresholds for monopolar, symmetric, and asymmetric H-FIRE pulses where the longest pulse was 1 µs. The (2, 1, 0.25) waveform had lethal thresholds of 594±32 and 818±25 V/cm for U87 and MDA cells, respectively, when energized for 100 µs per burst. These thresholds increased to 780±99 and 970±85 V/cm when the energized time was reduced to 50 µs.

The symmetric (2, 1, 2) waveform had lethal thresholds of 1316±43 and 1563±22 V/cm for U87 and MDA cells, respectively when bursts were energized for 100 µs. These thresholds increased to 1702±186 and 2028±63 V/cm when the energized time was reduced to 50 µs.

Across all treatment groups and cell types introducing asymmetry into the waveform by using a 0.5 µs pulse decreased the lethal threshold by 25% and using a 0.25 µs pulse decreased the lethal threshold by 45%, compared to the symmetric (1-1-1 or 2-1-2) waveforms. Use of a completely monopolar waveform decreased the lethal threshold by 56% compared to the symmetric waveforms. In contrast, increasing the energized time from 50 µs to 100 µs only decreased the lethal threshold by 20% across all treatment groups.

Reversible Electroporation Thresholds

FIGS. 12A-D illustrate that pulse waveforms can be used to tune reversible and irreversible electroporation responses. The figures show examination of reversible (RE, hashed) and irreversible (IRE, solid) thresholds in 2D monolayer cultures for different 50 µs protocols. In each group of bars in the graphs, the first two bars show U87 treatment groups and the second two show MDA treatment groups. Each received 100× bursts where each burst was energized for 50 µs. In general, reversible electroporation thresholds observed immediately after treatment were lower than the lethal thresholds observed 24 hours post treatment.

Figure 12A:
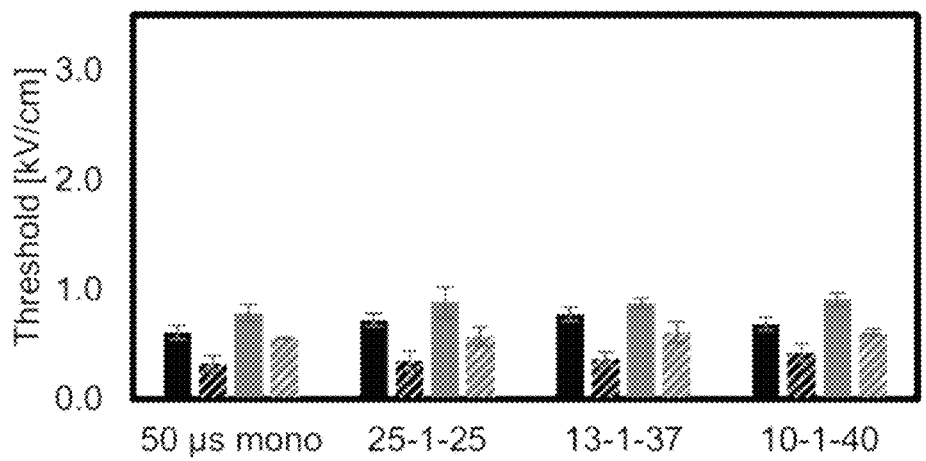
FIGS. 12A-D are bar graphs illustrating that pulse waveforms can be used to tune reversible and irreversible electroporation responses, according to principles of the present invention.

For long duration pulses, the reversible electroporation threshold was 40% (303 V/cm) lower than the lethal threshold across all cell types and waveforms. FIG. 12A is a bar graph showing RE and IRE thresholds for long duration (>20 µs) IRE pulses which were either monopolar (50 µs) or alternated with a 1 µs delay between polarity change. The 13-1-37 µs waveform resulted in the largest difference (407 V/cm) for U87 and the 25-1-25 µs waveform resulted in the largest difference (310 V/cm) for MDA cells.

Figure 12B:
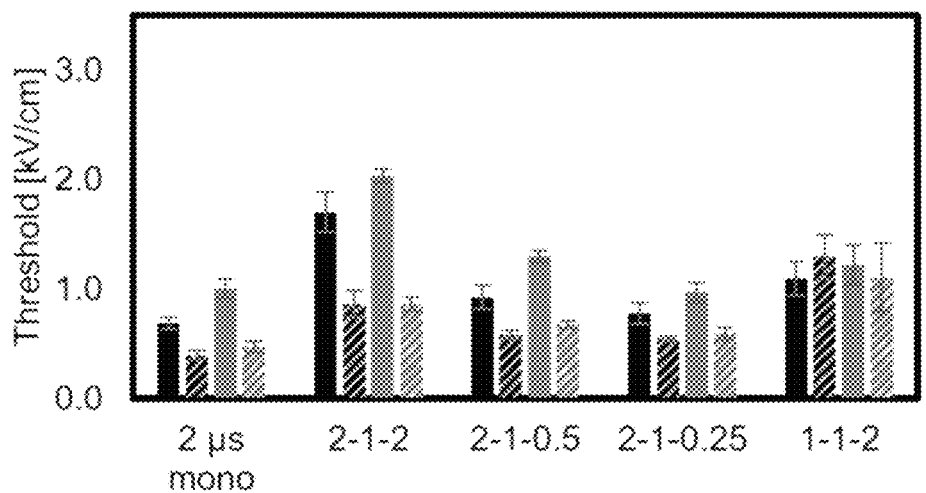
Figure 12C:
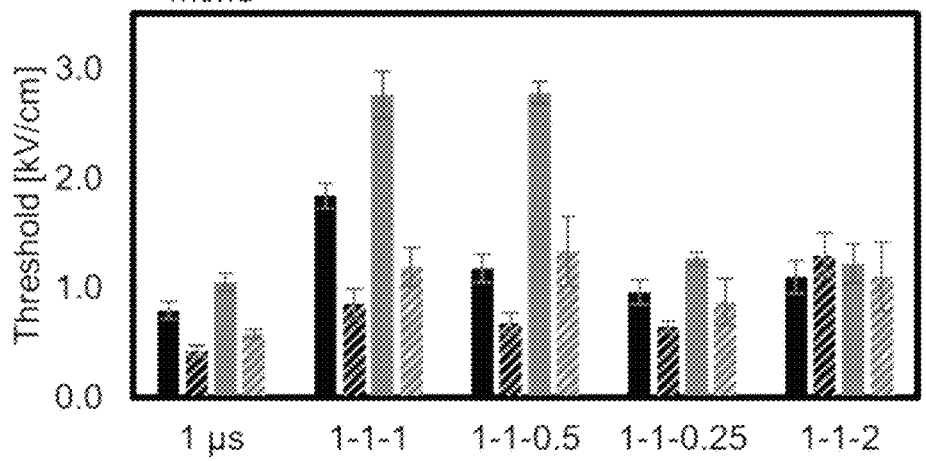
Figure 12D:
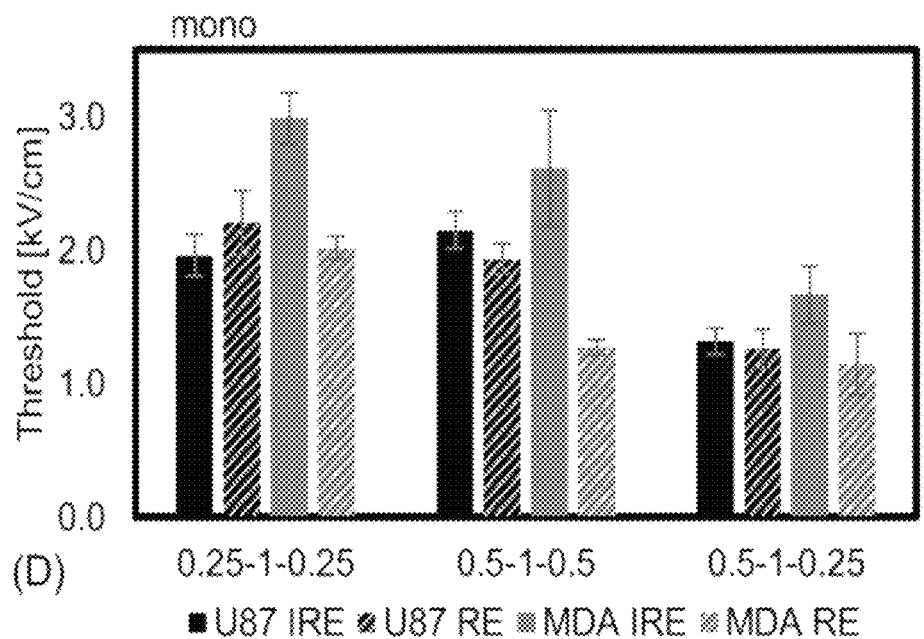

For H-FIRE waveforms, the largest differences between reversible and lethal thresholds occurred for the (1, 1, 1) and (2, 1, 2) symmetric bipolar waveforms. FIG. 12C is a bar graph showing RE and IRE thresholds for monopolar, symmetric, and asymmetric H-FIRE pulses where the longest pulse was 1 µs. FIG. 12D is a bar graph showing RE and IRE thresholds for monopolar, symmetric, and asymmetric H-FIRE pulses where the longest pulse was 0.5 µs.

For 2 µs H-FIRE waveforms (FIG. 12B) the reversible electroporation threshold was 44% lower than the lethal threshold averaged across all cell types and waveforms. FIG. 12B is a bar graph showing RE and IRE thresholds for monopolar, symmetric, and asymmetric H-FIRE pulses where the longest pulse was 2 µs. The (2, 1, 2) waveform resulted in the largest difference for U87 (837 V/cm, 49%) and MDA (1164 V/cm, 57%) cells. Interestingly, there was not a statistically significant difference in reversible and lethal thresholds for the (1, 1, 2) waveform for either cell type. The average threshold for this waveform was 1179 V/cm. In the 2 µs group, the lowest reversible electroporation thresholds were found for the monopolar waveform (U87=400 V/cm, MDA=476 V/cm).

For 1 µs H-FIRE waveforms (FIG. 12C) the reversible electroporation threshold was 45% lower than the lethal threshold averaged across all cell types and waveforms. The (1, 1, 1) waveform resulted in the largest difference for U87 (992 V/cm, 54%) and MDA (1572 V/cm, 57%) cells. In the 1 µs group, the lowest reversible electroporation thresholds were found for the monopolar waveform (U87=422 V/cm, MDA=579 V/cm). Sub-microsecond H-FIRE protocols were also evaluated (FIG. 12D). For U87 cells there was no statistically significant difference between the reversible and irreversible electroporation thresholds for the (0.25, 1, 0.25), (0.5, 1, 0.5), and (0.5, 1, 0.25) waveforms, however, the MDA cells did exhibit a significant difference for these waveforms. As with the 2 µs and 1 µs groups, the symmetric waveforms generally had higher reversible thresholds than the asymmetric waveforms.

Impact of Pulse Symmetry on Clinical Ablations

Figure 13A:
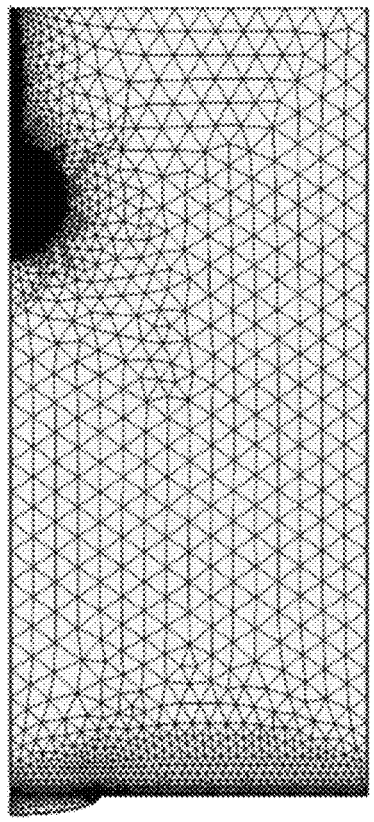
FIG. 13A shows a finite element mesh used to calculate the electric field distribution within a simulated tissue domain, according to principles of the present invention.
Figure 13B:
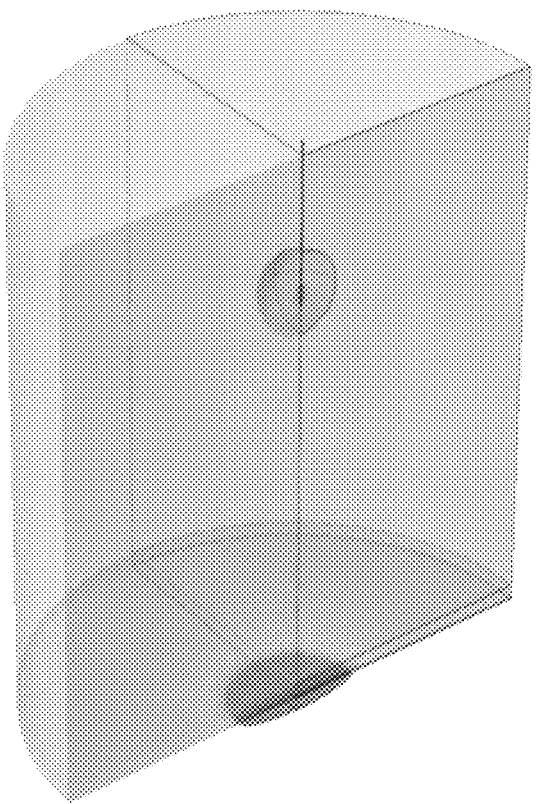
FIG. 13B shows a voltage distribution during pulse delivery when 3 kV is applied between the electrode and grounding pad, according to principles of the present invention.

To demonstrate the impact of different waveforms on clinical outcomes, a finite element model was created to simulate the ablation zones which would be created by the experimentally determined reversible and lethal thresholds. This model uses a single 1 cm needle and distal grounding pad separated by 30 cm, as illustrated in FIGS. 13A-B. The model calculates the electric field distribution around the electrode when 3000 V pulses are delivered. FIG. 13A shows a finite element mesh used to calculate the electric field distribution within a simulated tissue domain using a single 1 cm long, 1 mm diameter needle electrode and distal grounding pad. FIG. 13B shows a voltage distribution during pulse delivery when 3 kV is applied between the electrode and grounding pad.

Figures 13C, 13D:
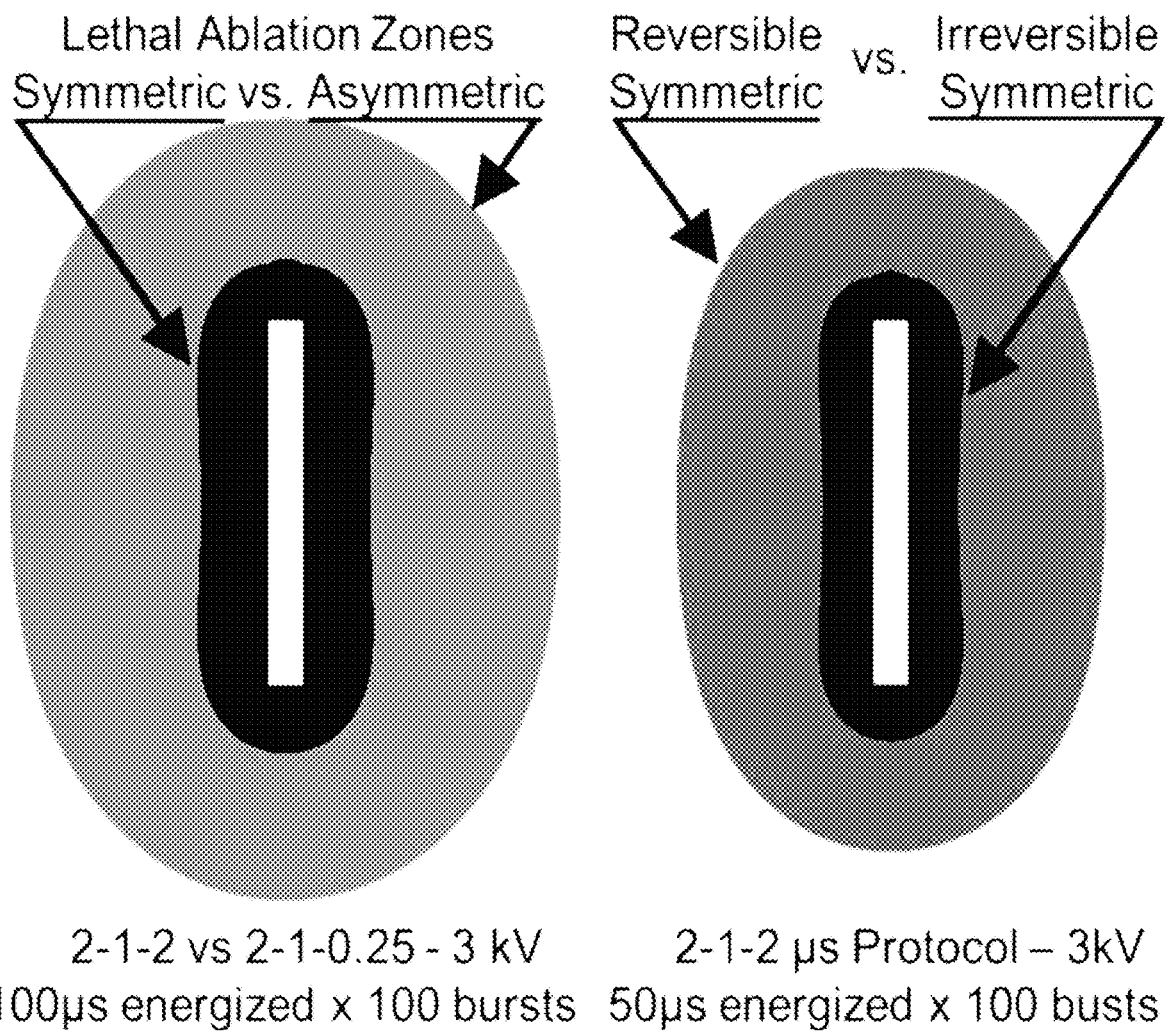
FIG. 13C shows a comparison of lethal ablation zones using the asymmetric and symmetric pulses, according to principles of the present invention.
FIG. 13D shows a comparison of the lethal ablation zone to the reversible electroporation zone, illustrating principles of the present invention.

Symmetric waveforms resulted in significantly higher lethal thresholds compared to asymmetric waveforms. Examples of the ablations created by the (2, 1, 2) and (2, 1, 0.25) waveforms are shown in FIG. 13C for protocols which use 100× bursts each energized for 100 µs. The symmetric waveform produces a small 1.4×0.5 cm oval shaped ablation zone. In contrast, the asymmetric waveform produces a significantly larger 2.2×1.6 cm ablation. FIG. 13C shows a comparison of lethal ablation zones using the asymmetric 2 µs lethal threshold (2, 1, 0.25), 590 V/cm, orange, and the symmetric 2 µs lethal threshold (2, 1, 2), 1320 V/cm, white, found for U87 cells in the 100 µs treatment group.

Interestingly, the symmetric waveforms exhibited the largest difference between reversible and lethal thresholds. An example of the reversible electroporation and lethal ablation zone predicted for the 2-1-2 waveform is shown in FIG. 13D for protocols which use 100× bursts each energized for 50 µs. The reversible electroporation zone is a relatively large 1.1×1.9 cm oval which surrounds a smaller 0.4×1.3 cm lethal zone. FIG. 13D shows a comparison of the lethal ablation zone (2-1-2, 1700 V/cm, white) to the reversible electroporation zone (2, 1, 2), 870 V/cm, orange, found for symmetric 2 µs H-FIRE bursts for U87 cells in the 50 µs treatment group.

Figure 14A:
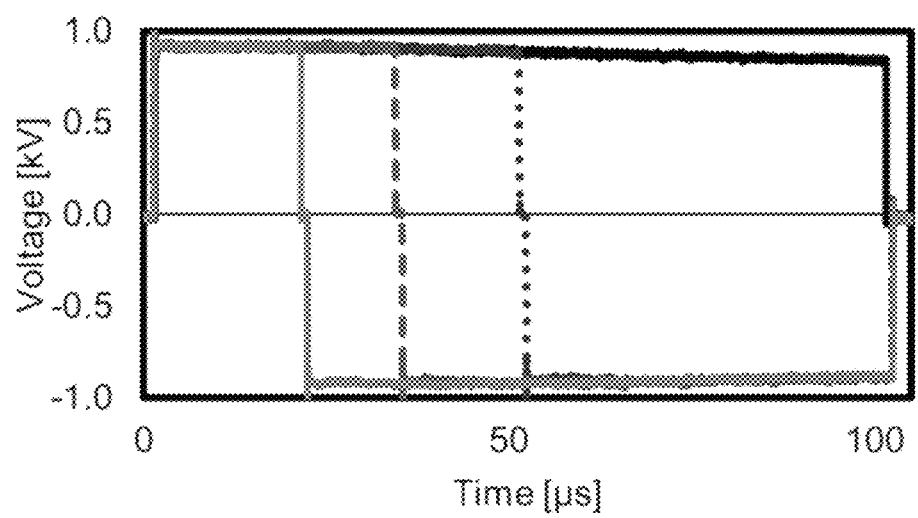
FIGS. 14A-D show bar graphs of voltage vs. time for several experimental waveforms, according to principles of the present invention.
Figure 14B:
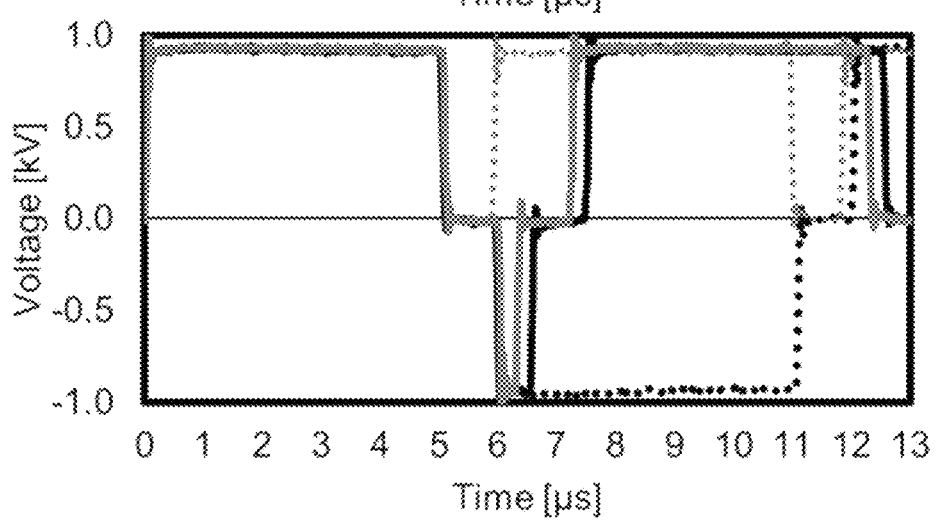
Figure 14C:
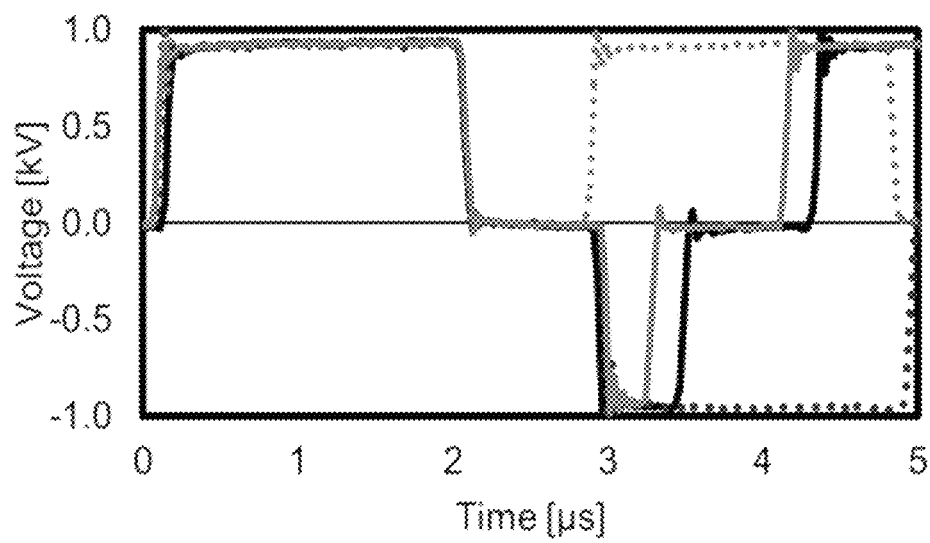
Figure 14D:
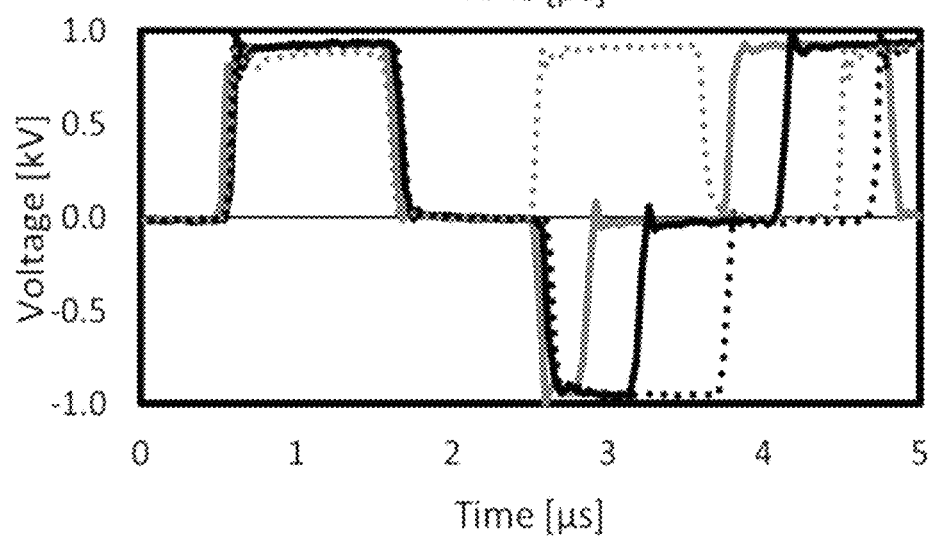

FIGS. 14A-D show graphs of voltage vs. time for several experimental waveforms. These waveforms demonstrate the ability of the H-Bridge topology (FIG. 5) to create a plurality of waveforms. FIG. 14A shows how the rail voltage can droop over individual pulses (or bursts) if large currents are delivered to the load. Increasing the total capacitance of the energy storage capacitor bank (FIG. 6) by adding additional capacitors in parallel will reduce this droop and enable the delivery of higher sustained currents. Waveforms in FIGS. 14B-D are repeated until the total energized time was equivalent to 50 or 100 µs. FIG. 14A shows long duration waveforms including a single 100 µs monopolar pulse and bipolar pulses (50, 1, 50), (33, 1, 67), and (20-1-80). FIG. 14B shows alternating polarity waveforms including a (5, 1, 0.25) pulse, a (5, 1, 0.5) pulse, and a (5, 1, 5) pulse. FIG. 14C shows waveforms including a 2 µs monopolar waveform and (2, 1, 2), (2, 1, 0.5), (2, 1, 0.25) bipolar bust waveforms. FIG. 14D shows waveforms including a 1 µs monopolar waveform and (1, 1, 1), (1, 1, 0.5), and (1, 1, 0.25) bipolar bust waveforms.

Discussion

H-FIRE is a relatively new electroporation protocol. Symmetric waveforms have been suggested as a method for creating more uniform ablations in heterogeneous tissues. Early in vitro experiments on cells in suspension showed that these waveforms required substantially higher electric fields (2-2.7×) to induce cell death versus the standard 100 µs monopolar IRE waveforms. When cells were grown in 3D collagen tumor models, the lethal electric field threshold decreased to 1.5× and 2.2× the IRE threshold for equivalent energy 2 µs and 1 µs symmetric H-FIRE protocols, respectively. This decrease is likely due to cells transforming from a spherical shape in suspension into a more natural geometry when cultured in 3D models.

Previous work found a lethal threshold of 500 V/cm for pancreatic cancer cells when delivering 80×100 µs monopolar IRE pulses in this 3D model. Here we found lethal thresholds for U87 brain cancer cells of 463 V/cm and 505 V/cm in 3D and 2D models, respectively, when 100×100 µs monopolar IRE pulses were delivered. Previous studies found lethal thresholds in liver tissue between 300 and 640V/cm using similar IRE protocols, indicating that both the 2D and 3D culture models recapitulate effects seen in mammalian tissue. Eleven of sixteen protocols conducted in 2D and 3D conditions showed no statistically significant difference in lethal threshold indicating that the 3D model has a limited effect on the lethal threshold and cells cultured in a 2D monolayer are a relatively effective model for studying H-FIRE. 2D monolayers are a convenient model as they are relatively simple to generate, are less expensive, and less time intensive to create compared to 3D cultures. However, when the thresholds were statistically different between groups, the 3D cultures all had lower lethal thresholds. This indicates that further investigation in 3D constructs may be warranted, especially if in vivo results are found to differ significantly from those found in 2D monolayers.

For all IRE and H-FIRE protocols, the lethal thresholds for U87 were lower than for MDA-MB-231 cells. Across all groups shown in FIGS. 11A-C, the mean thresholds were 36% lower for U87 cells. The largest difference observed (137%) was for the (1, 1, 0.5) waveform when 100×50 µs bursts were delivered. The smallest difference (13%) was observed for the (33, 1, 17) waveform. The 50 and 100 µs IRE groups (FIG. 11A) had the smallest average difference in lethal threshold between cell types at 26% across all waveforms. The average difference between cell types increased to 31% and 49% for 2 µs (FIG. 11B) and 1 µs (FIG. 11C) waveforms, respectively. While not extensively examined here, this may be due to differences in cell geometry affecting the charging time of the cell membrane.

For H-FIRE, waveform asymmetry appears to be the biggest factor affecting the lethal threshold. Doubling the dose delivered by energizing the burst for 100 µs rather than 50 µs decreased the lethal threshold by an average of 20%. In contrast, the lethal thresholds for asymmetric waveforms was 42% lower than the symmetric waveforms, averaged across all H-FIRE groups.

Waveforms incorporating a 0.5 µs or 0.25 µs pulses were 25% and 45% lower than symmetric waveforms, respectively. When only positive 1 µs or 2 µs pulses were used in the burst, the lethal thresholds were 56% lower on average compared to their respective symmetric (1, 1, 1) or (2, 1, 2) counterparts.

We hypothesize that there are two potential mechanisms which may be driving the decrease in lethal threshold when asymmetric waveforms are used. Electrokinetic transport may be increasing transport of charged molecules across the cell membrane resulting in conditions which make it challenging for the cell to regain homeostasis. This could potentially be investigated by introducing membrane impermeable particles into the culture media and tracking intracellular particle densities during and after electroporation. Alternatively, the asymmetric pulses may result in a slow cumulative charging of the transmembrane potential. This could potentially be investigated by using H-FIRE bursts which are energized for shorter durations (e.g. 10, 20, and 30 µs) and evaluating if lethal effects are amplified at a critical duration.

From a clinical prospective, asymmetric H-FIRE waveforms can potentially be used to produce equivalent ablation volumes to standard IRE protocols. Here we calculated an ablation volume of 0.17 cm$^3$ for a 3 kV treatment using lethal thresholds for the (2, 1, 2) waveform energized for 100 µs. In contrast, switching to a (2, 1, 0.25) waveform would increase the ablation volume 17-fold to 2.91 cm$^3$. A key motivation for switching from monopolar IRE pulses to H-FIRE waveforms is to mitigate the muscle contractions caused in vivo by the long duration pulses and extensive in vivo investigation will be necessary to evaluate if muscle contractions are present when asymmetric waveforms are used.

Waveform symmetry also has a large effect on the difference between reversible and lethal thresholds. Symmetric H-FIRE waveforms had a 54% difference between the reversible and lethal thresholds. This difference decreased to an average of 33% across all asymmetric H-FIRE waveforms evaluated. The maximum difference of 57% was observed for the (2, 1, 2) waveform in MDA cells and the minimum difference of 4% was observed for the (0.5, 1, 0.25) waveform in U87 cells. We calculated a lethal ablation zone of 0.1 cm$^3$ for a 3 kV treatment using the MDA lethal threshold for a 50μ (2, 1, 2) waveform. The 1.96 cm$^3$ reversible electroporation zone was 19 fold larger than the lethal zone.

From a clinical prospective, symmetric waveforms may be more advantageous in electro-chemotherapy (ECT) and electro-gene (EGT) protocols where the intent is to transfer membrane impermeable material into the cell rather than inducing cell death. Symmetric bipolar wave forms were recently reported to be an effective means for transiently disrupting the blood brain barrier, however, reversible electroporation for chemotherapy and gene transfer have yet to be demonstrated with these waveforms. Typical ECT and EGT protocols use 2 to 24 monopolar pulses between 100 μs and 20 ms to electroporate cells and electrophoretically drive molecules into cells. We hypothesize that protocols with a similar number of asymmetric bursts could potentially be used to achieve the same effect without producing large lethal ablation zones or inducing muscle contractions. However, further work will be necessary to determine optimal protocols for using H-FIRE waveforms for ECT/EGT.

CONCLUSION

In vitro models of primary and metastatic brain cancer were used to show that the lethal threshold for H-FIRE treatments is affected by the symmetry of the waveform. Asymmetric waveforms, including positive only polarity waveforms, have significantly lower lethal thresholds than equivalent energy symmetric waveforms. The use of asymmetric H-FIRE waveforms clinically should result in the creation of equivalent ablation volumes to those seen in IRE procedures while mitigating muscle contractions caused by long duration pulses. Interestingly, symmetric waveforms exhibited a large difference between reversible and lethal thresholds which may be useful for EGT and ECT protocols where maintaining tissue viability post-treatment is desired.

The invention claimed is:

1. A method for electroporation, the method comprising:
    selecting a desired treatment size for an ablation therapy treatment zone;
    inserting one or more therapeutic source electrodes into a target tissue;
    placing one or more sink electrodes in contact with the target tissue;
    selecting automatically by a computer an asymmetric bipolar pulse waveform that has positive pulses and negative pulses with different durations, wherein the computer computes a ratio of durations of the positive pulses and the negative pulses from the desired treatment size such that the ratio varies with the desired treatment size;
    delivering to the target tissue a series of electrical pulses having the selected asymmetric bipolar pulse waveform;
    whereby the desired treatment size for the ablation treatment zone may be controlled to either minimize or enhance ablation of cells in the target tissue.

2. The method of claim 1 wherein selecting an asymmetric bipolar pulse waveform comprises selecting an energy delivered in each burst, and a number of bursts delivered.

3. The method of claim 1 wherein selecting an asymmetric bipolar pulse waveform comprises computing voltage magnitudes for the positive pulses and the negative pulses.

4. The method of claim 1 wherein selecting an asymmetric bipolar pulse waveform comprises selecting an asymmetric waveform whose positive and negative pulses have different voltage magnitudes, wherein the computer computes the voltage magnitudes of the positive pulses and the negative pulses from the desired treatment size.

5. The method of claim 1 further comprising: selecting a desired treatment size for a reversible treatment zone; introducing an electroporation compound into the target tissue; and wherein the computer computes asymmetric bipolar pulse waveform parameters based on the desired treatment size for the reversible treatment zone.

6. An apparatus for electroporation, the apparatus comprising:
    therapeutic electrodes for insertion into a target tissue;
    a computer controller for generating an asymmetric bipolar pulse waveform that has positive pulses and negative pulses with different durations, wherein the computer controller computes a ratio of durations of the positive pulses and the negative pulses from a desired treatment size for an ablation therapy treatment zone such that the ratio varies with the desired treatment size;
    a hardware controller for generating high voltage electrical pulses to the therapeutic electrodes in accordance with the generated asymmetric bipolar pulse waveform; such that the desired treatment size for the ablation treatment zone may be controlled to either minimize or enhance ablation of cells in the target tissue.

7. The apparatus of claim 6 comprising a high voltage switching circuit comprising four switches to create an H-Bridge configuration for delivering positive and negative polarity pulses from a single high voltage power supply.

8. The apparatus of claim 6 comprising two switches in a totem pole configuration for delivering positive and negative polarity pulses from a positive and negative power supply.

9. The apparatus of claim 6 comprising a transformer in conjunction with an H-Bridge or totem pole configuration to step up a lower voltage to a higher voltage.

10. The apparatus of claim 6 further comprising a capacitor bank comprising switches, wherein each switch is made up of two or more components in parallel and two or more components in series to increase the voltage and current that each switch can deliver.

11. The apparatus of claim 6 comprising a high voltage source connected to a capacitor bank of one or more capacitors in a series-parallel arrangement.

12. The apparatus of claim 6 comprising a high voltage source connected to a single high voltage capacitor.

* * * * *

UNITED STATES PATENT AND TRADEMARK OFFICE
CERTIFICATE OF CORRECTION

PATENT NO. : 10,589,092 B2
APPLICATION NO. : 15/616737
DATED : March 17, 2020
INVENTOR(S) : Michael Sano It is certified that error appears in the above-identified patent and that said Letters Patent is hereby corrected as shown below:

In the Specification

At Column 1, Line 13, insert the following:
--STATEMENT OF GOVERNMENT SPONSORED SUPPORT
This invention was made with Government support under contract W81XWH-15-1-0137 awarded by the Department of Defense. The Government has certain rights in the invention.--

Signed and Sealed this
Third Day of September, 2024

Katherine Kelly Vidal
*Director of the United States Patent and Trademark Office*